United States Patent
Ma et al.

(10) Patent No.: US 9,732,112 B2
(45) Date of Patent: Aug. 15, 2017

(54) SYNTHESIS OF 2',3'-DIDEOXYNUCLEOSIDES FOR AUTOMATED DNA SYNTHESIS AND PYROPHOSPHOROLYSIS ACTIVATED POLYMERIZATION

(71) Applicant: LIFE TECHNOLOGIES CORPORATION, Carlsbad, CA (US)

(72) Inventors: Zhaochun Ma, Sunnyvale, CA (US); Khairuzzaman Bashar Mullah, Union City, CA (US); Robert G. Eason, Los Gatos, CA (US)

(73) Assignee: Life Technologies Corporation, Carlsbad, CA (US)

(*) Notice: Subject to any disclaimer, the term of this patent is extended or adjusted under 35 U.S.C. 154(b) by 59 days.

(21) Appl. No.: 14/952,149

(22) Filed: Nov. 25, 2015

(65) Prior Publication Data

US 2016/0108079 A1    Apr. 21, 2016

Related U.S. Application Data

(62) Division of application No. 14/173,725, filed on Feb. 5, 2014, now Pat. No. 9,228,227, which is a division of application No. 13/117,029, filed on May 26, 2011, now Pat. No. 8,658,776.

(60) Provisional application No. 61/349,791, filed on May 28, 2010, provisional application No. 61/352,197, filed on Jun. 7, 2010.

(51) Int. Cl.

| C07H 19/06 | (2006.01) |
|---|---|
| C07H 19/16 | (2006.01) |
| C07D 473/34 | (2006.01) |
| C07D 405/04 | (2006.01) |
| C07D 473/18 | (2006.01) |
| C07D 239/54 | (2006.01) |
| C07H 21/00 | (2006.01) |
| C07H 21/02 | (2006.01) |
| C07H 21/04 | (2006.01) |
| C12Q 1/68 | (2006.01) |

(52) U.S. Cl.
CPC ........... *C07H 19/16* (2013.01); *C07D 239/54* (2013.01); *C07D 405/04* (2013.01); *C07D 473/18* (2013.01); *C07D 473/34* (2013.01); *C07H 19/06* (2013.01); *C07H 21/00* (2013.01); *C07H 21/02* (2013.01); *C07H 21/04* (2013.01); *C12Q 1/6806* (2013.01)

(58) Field of Classification Search
None
See application file for complete search history.

(56) References Cited

U.S. PATENT DOCUMENTS

| 4,683,195 | A | 7/1987 | Mullis et al. |
|---|---|---|---|
| 4,683,202 | A | 7/1987 | Mullis |
| 4,889,818 | A | 12/1989 | Gelfand et al. |
| 4,965,188 | A | 10/1990 | Mullis et al. |
| 5,035,996 | A | 7/1991 | Hartley |
| 5,079,352 | A | 1/1992 | Gelfand et al. |
| 5,210,015 | A | 5/1993 | Gelfand et al. |
| 5,436,134 | A | 7/1995 | Haugland et al. |
| 5,487,972 | A | 1/1996 | Gelfand et al. |
| 5,538,848 | A | 7/1996 | Livak et al. |
| 5,618,711 | A | 4/1997 | Gelfand et al. |
| 5,658,751 | A | 8/1997 | Yue et al. |
| 5,677,152 | A | 10/1997 | Birch et al. |
| 5,723,591 | A | 3/1998 | Livak et al. |
| 5,773,258 | A | 6/1998 | Birch et al. |
| 5,789,224 | A | 8/1998 | Gelfand et al. |
| 5,801,155 | A | 9/1998 | Kutyavin et al. |
| 5,804,375 | A | 9/1998 | Gelfand |
| 5,854,033 | A | 12/1998 | Lizardi |
| 5,876,930 | A | 3/1999 | Livak et al. |
| 5,994,056 | A | 11/1999 | Higuchi |
| 6,030,787 | A | 2/2000 | Livak et al. |
| 6,084,102 | A | 7/2000 | Kutyavin et al. |
| 6,127,155 | A | 10/2000 | Gelfand et al. |
| 6,171,785 | B1 | 1/2001 | Higuchi |
| 6,214,979 | B1 | 4/2001 | Gelfand et al. |
| 6,258,569 | B1 | 7/2001 | Livak et al. |
| 6,814,934 | B1 | 11/2004 | Higuchi et al. |
| 6,821,727 | B1 | 11/2004 | Livak et al. |
| RE39,007 | E | 3/2006 | Dattagupta |
| 7,033,763 | B2 | 4/2006 | Liu et al. |

(Continued)

FOREIGN PATENT DOCUMENTS

| EP | 0070685 | 1/1983 |
|---|---|---|
| WO | 94/16108 | 6/1994 |

(Continued)

OTHER PUBLICATIONS

Liu et al., "Pyrophosphorolysis-Activated Polymerization (PAP): Application to Allele-Specific Amplification" BioTechniques (2000) vol. 29 No. 5 1072-1083.*

Afonina, I.A. et al., "Minor Groove Binder-Conjugated DNA Probes for Quantitative DNA Detection by Hybridization-Triggered Fluorescence", *BioTechniques*, vol. 32, 2002, 940-949.

Baner, Johan et al., "Signal Amplification of PadlockProbes by Rolling Circle Replication,", *Nucleic Acids Research*, vol. 26, No. 22, 1998, 5073-5078.

Barany, et al., "Genetic Disease Detection and DNA Amplification Using Cloned Thermostable Ligase", *Proceedings of the National Academy of Sciences*, vol. 88, Issue 1, 1991, 189-193.

(Continued)

*Primary Examiner* — Eric Olson
(74) *Attorney, Agent, or Firm* — McNeill Baur PLLC

(57) ABSTRACT

Methods for preparation of 2',3'-dideoxynucleotides support structures, such as 2',3'-dideoxyguanosine, 2',3'-dideoxyadenosine, and 3'-deoxythymidine support structures are disclosed. Various methods of using such structures are also provided, such as their use for automated DNA synthesis and pyrophosphorolysis activated polymerization.

15 Claims, No Drawings

(56) References Cited

U.S. PATENT DOCUMENTS

| | | |
|---|---|---|
| 7,141,377 B2 | 11/2006 | Gelfand et al. |
| 7,445,900 B2 | 11/2008 | Gelfand et al. |
| 2004/0038215 A1 | 2/2004 | Kumar et al. |
| 2004/0265897 A1 | 12/2004 | Lizardi |
| 2005/0009054 A1 | 1/2005 | Phillion et al. |
| 2009/0197254 A1 | 8/2009 | Lee |

FOREIGN PATENT DOCUMENTS

| | | |
|---|---|---|
| WO | 00/60121 | 10/2000 |
| WO | 2005/081222 | 8/2006 |
| WO | 2006/087574 | 8/2006 |
| WO | 2011/150277 | 12/2011 |

OTHER PUBLICATIONS

Cardullo, Richard A. et al., "Detection of Nucleic Acid Hybridization by Non Radiative Fluorescence Resonance Energy Transfer", *Proceedings of the National Academy of Sciences (PNAS)*, vol. 85, 1988, 8790-8794.

Fiandaca, Mark J. et al., "Self-Reporting PNA/DNA Primers for PCR Analysis", *Genome Research*, vol. 11, 2001, 609-613.

French, D.J. et al., "HyBeacon™ Probes: A New Tool for DNA Sequence Detection and Allele Discrimination", *Molecular and Cellular Probes*, vol. 15, 2001, 363-374.

Glick, Gary D., "Synthesis of a Conformationally Restricted DNA Hairpin", *Journal of Organic Chemistry*, vol. 56, No. 24, 1991, 6746-6747.

Hughes, Randall A. et al., "Gene Synthesis: Methods and Applications", *Methods in Enzymology, Chapter Twelve*, vol. 498, 2011, 277-309.

Li, Qingge et al., "A New Class of Homogeneous Nucleic Acid Probes Based on Specific Displacement Hybridization,", *Nucleic Acids Research*, vol. 30, No. 2, e5, 2002, 1-9.

Little, Michael C., "Strand Displacement Amplification and Homogeneous Real-Time Detection Incorporated in a Second-Generation DNA Probe System, BDProbeTecET", *Clinical Chemistry*, vol. 45, No. 6, 1999, 777-784.

Lizardi, et al., "Mutation Detection and Single-Molecule Counting Using Isothermal Rolling-Circle Amplification", *Nature Genetics*, vol. 19, No. 3, Jul. 1998, 225-232.

Nazarenko, Irina et al., "Multiplex quantitative PCR using self quenched primers labeled with a single fluorophore", *Nucleic Acids Research*, vol. 30, No. 9, e37, 2002, 1-7.

Nazarenko, Irina A. et al., "A Closed Tube Format for Amplification and Detection of DNA Based on Energy Transfer", *Nucleic Acids Research*, vol. 25, No. 12, 1997, 2516-2521.

Nutiu, Razvan et al., "Tripartite Molecular Beacon,", *Nucleic Acids Research*, vol. 30, e94, 2002, 1-9.

Osborne, et al., "Incorporating Disulfide Cross-Links at the Terminus of Oligonucleotides Via Solid-Phase Nucleic Acid Synthesis", *Bioorganic & Medicinal Chemistry Letters*, vol. 6, No. 19, 1996, 2339-2342.

Oser, Andreas et al., "Nonradioactive Assay of DNA Hybridization by DNA-Template-Mediated Formation of a Ternary TbIII Complex in Pure Liquid Phase", *Angewandte Chemie International Edition in English*, vol. 29, No. 10, 1990, 1167-1169.

PCT/US2011038238; International Search Report and Written Opinion mailed Dec. 6, 2011, 14 Pgs.

Pellestor, Franck et al., "The Peptide Nucleic Acids (PNAs), Powerful Tools for Molecular Genetics and Cytogenetics", *European Journal of Human Genetics*, vol. 12, 2004, 694-700.

Singh, S. et al., "LNA (locked nucleic acids): synthesis and high-affinity nucleic acid recognition", *Chem. Commun.*, 1998, pp. 455-456.

Sram, J. et al., "Microarray-Based DNA Resequencing Using 3' Blocked Primers", *Analytical Biochemistry*, vol. 374, No. 1 ,, Mar. 2008, 41-47.

Stolze, Karen et al., "Synthesis of 3-Sugar- and Base-Modified Nucleotides and Their Application as Potent Chain Terminators in DNA Sequencing", *Helvetica Chimica Acta*, vol. 82, No. 9, 1999, 1311-1323.

Svanvik, Nicke et al., "Light-Up Probes: Thiazole Orange-Conjugated Peptide Nucleic Acid for Detection of Target Nucleic Acid in Homogeneous Solution", *Analytical Biochemistry*, vol. 281, 2000, 26-35.

Todd, Alison V. et al., "DzyNA-PCR: Use of DNAzymes to Detect and Quantify Nucleic Acid Sequences in a Real-Time Fluorescent Format", *Clinical Chemistry*, vol. 46, No. 5, 2000, 625-630.

Tyagi, et al., "Molecular Beacons: Probes that Fluoresce upon Hybridization", *Nature Biotechnology*, vol. 14, No. 3, Mar. 1996, 303-308.

Waldvogel, S. et al., "Nucleotides. Part 55. Synthesis and Application of a Novel Linker for Solid-Phase Synthesis of Modified Oligonucleotides", *Helvetica Chimica Acta*, vol. 81, Jan. 1, 1998, pp. 46-58.

Whitcombe, David et al., "Detection of PCR products using self-probing amplicons and fluorescence", *Nature Biotechnology*, vol. 17, Aug. 1999, 804-807.

Wu, Dan Y. et al., "The Ligation Amplification Reaction (LAR)-Amplification of Specific DNA Sequences Using Sequential Rounds of Template-Dependent Ligation," *Genomics*, vol. 4, 1989, 560-569.

\* cited by examiner

SYNTHESIS OF 2',3'-DIDEOXYNUCLEOSIDES FOR AUTOMATED DNA SYNTHESIS AND PYROPHOSPHOROLYSIS ACTIVATED POLYMERIZATION

CROSS-REFERENCE TO RELATED APPLICATIONS

This application is a divisional of U.S. patent application Ser. No. 14/173,725 filed Feb. 5, 2014, now U.S. Pat. No. 9,228,227, which is a divisional application of U.S. patent application Ser. No. 13/117,029, filed May 26, 2011, now U.S. Pat. No. 8,658,776, which claims the benefit of priority under 35 U.S.C. §119(e) to U.S. Provisional Patent Application Nos. 61/349,791, filed May 28, 2010 and 61/352,197, filed Jun. 7, 2010, which are herein incorporated by reference in their entirety.

FIELD

This invention relates generally to the field of nucleic acid polymerization and amplification. More specifically, this invention relates to methods of synthesis of various 2',3'-dideoxynucleoside supports, such as 2',3'-dideoxyguanosine, 2',3'-dideoxyadenosine, 3'-deoxythymidine and 2',3'-dideoxyuridine supports, and to their use.

BACKGROUND

Pyrophosphorolysis-activated polymerization (PAP) is a technique useful for nucleic acid polymerization and amplification. PAP is an allele-specific amplification method, the essence of which is that 3'-dideoxynucleotide-terminated primers (also designated as "P*") are activated with a specific polymerase enzyme, in the presence of pyrophosphate (also designated as "PPi"). As a result, the P* primer is hybridized with the complementary target sequence.

Accordingly, PAP allows one to obtain a desired nucleic acid strand on a nucleic acid template strand. This is useful for detecting rare mutations with high selectivity. PAP is a promising technology in the field of cancer diagnostics, genotoxicology, amplification with increased specificity, nucleic acid synthesis, and other applications.

Some features of PAP have been described previously. See, e.g., U.S. Pat. No. 7,033,763 to Liu et al., the contents of which are incorporated herein by reference in its entirety. Briefly, the PAP method serially couples pyrophosphorolysis with polymerization by DNA polymerase for each amplification by using an activatable oligonucleotide P* that has a non-extendible 3'-deoxynucleotide at its 3' terminus PAP can be applied for exponential amplification or for linear amplification.

The basic steps of the PAP process involve annealing to a nucleic acid an oligonucleotide P* having a non-extendable 3' end. The 3' non-extendable terminus of the oligonucleotide P* is removed by pyrophosphorolysis and an unblocked oligonucleotide can be obtained as a result. Finally, the unblocked oligonucleotide can be extended and the presence of the nucleic acid can be detected by detecting the extended oligonucleotide. The chemistry involved in the process of pyrophosphorolysis is the reaction of pyrophosphate with a 3'-nucleotide monophosphate (NMP) which is removed from duplex DNA.

While PAP is undoubtedly a very attractive technique, it has certain deficiencies and drawbacks. One difficulty lies in the process of obtaining a suitable oligonucleotide P*. For instance, such products as ddA, ddG, and dT are not available commercially and have to be synthesized. Previously, the synthesis of those ddN-terminated oligonucleotides P* was conducted by using terminal transferase. Alternatively, 5'-to-3' reverse synthesis was employed, using 2',3'-ddA, 2',3'-ddG or 2',3'-ddT CE phosphoroamidite, dA-5', dT-5', dG-5', or dC-5' CE phosphoroamidite, and 5'-dA, dG, dC or dT support. All such synthetic methods are labor intensive and costly.

For dT, the most favorable point of attachment is via the N3 imino nitrogen on the pyrimidine ring, but no N3-protected derivative of 3'-deoxythymidine is available or has been described. Likewise, no adequate method for making a DNA containing dT has been described, other than expensive 5'-to-3' reverse synthesis. This is likely due to the fact that there is a lack of convenient exocyclic functional group for covalent linkage on the thymine base. Attachment via an exocyclic oxygen, such as 4-oxo, is possible, but alkoxides thus formed are known to be displaced from thymine by nitrogen nucleophiles, such as ammonia, which are used during oligonucleotide deprotection and cleavage. As a result, 3'-terminal thymine can convert to a cytidine derivative.

Accordingly, better methods are needed for preparing oligonucleotides P* suitable for the PAP process. Such methods would allow for easy synthesis of the oligonucleotides and labeled primers, without resorting to expensive 5'-amidite synthesis or to 5' to 3' reverse synthesis. The primers so produced would have all the beneficial properties of the primers obtainable by the above-described earlier methods, such as selectivity of PAP in allele-specific PCR. The instant specification describes such synthetic methods.

SUMMARY

The methods disclosed herein are useful for synthesizing various 2',3'-dideoxynucleoside supports, such as 2',3'-dideoxyguanosine, 2',3'-dideoxyadenosine, 3'-deoxythymidine and 2',3'-dideoxyuridine supports.

According to certain embodiments, methods for preparing 2',3'-dideoxyguanosine support structures are provided herein. Such methods comprise reacting 2',3'-dideoxyguanosine with N,N-dimethylformamide dimethylacetal, to obtain a first intermediate. Subsequently, the first intermediate is reacted with 4,4-dimethoxytriphenylmethyl chloride, to obtain a second intermediate. The dimethylformamide protecting group can then be cleaved off the second intermediate, and the resulting product is reacted with adipic anhydride to create a precursor for the 2',3'-dideoxyguanosine support structure. This precursor can then be coupled to a suitable solid support, such as long chain alkyl amine/controlled pore glass beads (LCAA-CPG), to obtain a 2',3'-dideoxyguanosine support structure.

According to other embodiments, methods for preparing 2',3'-dideoxyadenosine support structures are provided. Such methods comprise reacting 2',3'-dideoxyadenosine with 4,4-dimethoxytriphenylmethyl chloride, to obtain an intermediate, which can then be reacted with the product of the reaction between pentane-1,3,5-tricarboxylic acid and oxalyl chloride, to obtain a second intermediate. As a result, a precursor for the 2',3'-dideoxyadenosine support structure is obtained. This precursor can then be coupled to any suitable solid support, such as long chain alkyl amine/controlled pore glass beads, to obtain a 2',3'-dideoxyadenosine support structure.

According to other embodiments, methods for preparing 3'-deoxythymidine support structures are provided herein.

Such methods comprise esterifying 5-fluoro-2-nitrobenzoic acid, to obtain an ester intermediate, followed by reacting the ester intermediate with 2-mercaptoethanol, to obtain a thioether intermediate. A 5'-dimethoxytriphenylmethyl derivative of thymidine, i.e., 1-(5-((bis(4-methoxyphenyl)(phenyl)methoxy)methyl)tetrahydrofuran-2-yl)-5-methyl-pyrimidine-2,4-dione, can then be reacted with the thioether intermediate, under the Mitsunobu conditions, followed by saponification of the resulting product. As a result, a precursor for the 3'-deoxythymidine support structure is obtained. This precursor can then be coupled to a suitable solid support, such as aminopropylsilyl/controlled pore glass beads, to obtain a 3'-deoxythymidine support structure. This structure can then be optionally acylated to deactivate unreacted aminopropyl groups and then oxidized to convert the thioether to a sulfone.

According to other embodiments, methods for preparing an oligonucleotide labeled with 2',3'-dideoxyguanosine, an oligonucleotide labeled with 2',3'-dideoxyadenosine, or an oligonucleotide labeled with 3'-deoxythymidine are provided herein. Such methods include synthesizing a 2',3'-dideoxyguanosine support structure, a 2',3'-dideoxyadenosine support structure, or a 3'-deoxythymidine support structure. Any of these structures can then be used in an automated DNA synthesis method available in the art.

According to other embodiments, methods are provided herein for detecting a nucleic acid. Such methods comprise first preparing a 2',3'-dideoxynucleoside having a non-extendable 3' end which is removable by pyrophosphorolysis, such as 2',3'-dideoxyguanosine, 2',3'-dideoxyadenosine, and 3'-deoxythymidine. Any of these 2',3'-dideoxynucleosides can be prepared according to the methods provided herein. The 2',3'-dideoxynucleoside can be used to make a 2',3'-dideoxynucleotide which can be annealed to a nucleic acid. The 3' non-extendable terminus of the 2',3'-dideoxynucleotide can be removed by pyrophosphorolysis to produce an unblocked oligonucleotide. This unblocked oligonucleotide can be extended and the presence of the nucleic acid can be detected by detecting the extended oligonucleotide.

According to other embodiments, methods are provided herein for detecting a nucleic acid. Such methods comprise first preparing a 2',3'-dideoxynucleoside having a non-extendable 3' end which is removable by pyrophosphorolysis, such as 2',3'-dideoxyguanosine, 2',3'-dideoxyadenosine, 3'-deoxythymidine and 2',3'-dideoxyuridine. Any of these 2',3'-dideoxynucleosides can be prepared according to the methods disclosed herein. The 2',3'-dideoxynucleoside can be used to make a 2',3'-dideoxynucleotide which can be annealed to a nucleic acid. The 3' non-extendable terminus of the 2',3'-dideoxynucleotide can be removed by pyrophosphorolysis to produce an unblocked oligonucleotide. This unblocked oligonucleotide can be extended in the presence of a nucleic acid polymerase.

According to other embodiments, methods are provided herein for detecting a nucleic acid. Such methods comprise first preparing two different 2',3'-dideoxynucleosides each having a non-extendable 3' end, which is removable by pyrophosphorolysis, such as 2',3'-dideoxyguanosine, 2',3'-dideoxyadenosine, 3'-deoxythymidine or 2',3'-dideoxyuridine. Any of these 2',3'-dideoxynucleosides can be prepared according to the methods disclosed herein. The 2',3'-dideoxynucleoside can be used to make a 2',3'-dideoxynucleotide which can be annealed to a nucleic acid; the first 2',3'-dideoxynucleotides overlaps with the second 2',3'-dideoxynucleotide by at least one nucleotide at their respective 3' ends, and one of the 2',3'-dideoxynucleotides anneals to a first nucleic acid strand and the other 2',3'-dideoxynucleotide anneals to a nucleic acid strand which is the complement of the first nucleic acid strand. The 3' non-extendable terminus of the annealed first 2',3'-dideoxynucleotide and second 2',3'-dideoxynucleotide can be then removed by pyrophosphorolysis to obtain unblocked oligonucleotides, which can then be extended and detected.

According to other embodiments, methods are provided herein for detecting a nucleic acid. Such methods include synthesizing a template nucleic acid from the nucleic acid and preparing a 2',3'-dideoxynucleoside, such as 2',3'-dideoxyguanosine, 2',3'-dideoxyadenosine, 3'-deoxythymidine or 2',3'-dideoxyuridine. Any of these 2',3'-dideoxynucleosides can be prepared according to the methods disclosed herein. The 2',3'-dideoxynucleotide has a non-extendable 3' end which is removable by pyrophosphorolysis. The 2',3'-dideoxynucleoside can be used to make a 2',3'-dideoxynucleotide which can be annealed to the template nucleic acid, followed by removing the 3' non-extendable terminus of the 2',3'-dideoxynucleotide that is annealed to the template nucleic acid by pyrophosphorolysis. Thus, an unblocked oligonucleotide can be obtained and extended and the presence of the nucleic acid can be detected by detecting the extended oligonucleotide.

According to other embodiments, pyrophosphorolysis-activated polymerization methods are provided herein for synthesizing a desired nucleic acid strand on a nucleic acid template strand. These methods comprise preparing a 2',3'-dideoxynucleoside according to the methods disclosed herein, followed by converting it into an activatable 2',3'-dideoxynucleotide having a non-extendable 3'-deoxynucleotide end, which is removable by pyrophosphorolysis, and further having a mismatch with respect to the corresponding nucleotide on the template strand. The 2',3'-dideoxynucleotide can then be annealed to the template strand followed by pyrophosphorolysis of the resulting duplex with pyrophosphate and an enzyme that has pyrophosphorolysis activity, and then extending, in the presence of a polymerase, the activated 2',3'-dideoxynucleotide on the template strand.

These and other features of the methods disclosed herein will become better understood with reference to the following description, drawings, and appended claims.

DETAILED DESCRIPTION

Reference will now be made in detail to some embodiments of the methods disclosed herein. While the methods will be described in conjunction with the embodiments discussed below, it will be understood that they are not intended to limit the disclosure to those embodiments. On the contrary, the invention is intended to cover alternatives, modifications, and equivalents, which may be included within the methods as defined by the appended claims.

I. DEFINITIONS AND ABBREVIATIONS

Unless stated otherwise, the following terms, definitions, and abbreviations as used herein are intended to have the following meanings:

The term "nucleoside" refers to a compound consisting of a purine, deazapurine, or pyrimidine nucleoside base, i.e., adenine, guanine, cytosine, uracil, thymine, deazaadenine, deazaguanosine, and the like, linked to a pentose at the 1' position, including 2',3'-dideoxy forms.

The term "2',3'-dideoxynucleoside(s)" as used herein refers to 2',3'-dideoxyguanosine, 2',3'-dideoxyadenosine, 3'-deoxythymidine and 2',3'-dideoxyuridine and combinations thereof.

The term "nucleotide" as used herein refers to a phosphate ester of a nucleoside, e.g., triphosphate esters, wherein the most common site of esterification is the hydroxyl group attached to the $C_5$ position of the pentose.

The term "nucleoside" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine. As used herein, the term nucleoside is intended to include both nucleosides and nucleotides.

As used herein, the terms "polynucleotide" or "oligonucleotide" refer to linear polymers of natural nucleotide monomers or analogs thereof including double- and single-stranded deoxyribonucleotides, ribonucleotides, α-anomeric forms thereof, and the like. Usually the nucleoside monomers are linked by phosphodiester linkages. As used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Polynucleotides typically range in size from a few monomeric units, e.g. 8-40, to several thousands of monomeric units.

Whenever a polynucleotide is represented by a sequence of letters, such as "ATGCCTG," it will be understood that the nucleotides are in 5'→3' (i.e., 5'-to-3') order from left to right and that "A" denotes deoxyadenosine, "C" denotes deoxycytidine, "G" denotes deoxyguanosine, and "T" denotes thymidine, unless otherwise noted.

The term "pyrophosphorolysis-actived polymerization" (PAP) refers to an allele-specific amplification method, which is a reverse process of polymerization, wherein 3'-dideoxynucleotide-terminated primers are activated with a specific polymerase enzyme in the presence of pyrophosphate. Features of PAP have been described previously. See, e.g., U.S. Pat. No. 7,033,763, the content of which is incorporated herein by reference in its entirety.

The nucleic acid polymerase can be any compound or system that will function to accomplish the amplification of the nucleic acid. Suitable enzymes include, for example, Tfl DNA polymerase, Taq DNA polymerase, E. coli DNA polymerase I, Klenow fragment of E. coli DNA polymerase I, T4 DNA polymerase, T7 DNA polymerase, other available DNA polymerases, RNA polymerases or their variants, reverse transcriptase or its variants, and other genetically engineered versions, such as ThermoSequenase.

The symbol P* refers to a 3'-dideoxynucleotide-terminated primer.

The term pyrophosphate (PPi) refers to the anion $P_2O_7^{4-}$, which is an anion of pyrophosphoric acid, $(HO)_2$—P(O)—O—P(O)(OH)$_2$, or $P_2O_7H_4$. Pyrophosphoric acid can be considered to be a dimer of phosphoric acid $H_3PO_4$. Pyrophosphate can be formed in cells as a product of hydrolysis of adenosine 5'-triphosphate (ATP), producing adenosine 5'-monophosphate (AMP) and PPi.

The chemical name "2',3'-dideoxyguanosine" refers to a compound where guanine is linked to a pentose at the $C_1$ position of the pentose and where the pentose lacks hydroxyl groups in both the $C_2$ position and $C_3$ position. The compound has the formula:

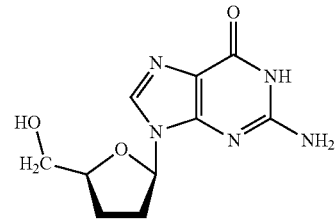

The chemical name "2',3'-dideoxyadenosine" refers to a compound where adenine is linked to a pentose at the $C_1$ position of the pentose and where the pentose lacks hydroxyl groups in both the $C_2$ position and $C_3$ position. The compound has the formula:

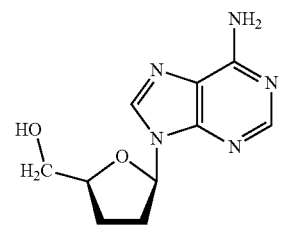

The chemical name "3'-deoxythymidine" refers to a compound where thymine is linked to a pentose at the $C_1$ position of the pentose and where the pentose lacks hydroxyl groups in the $C_3$ position. The compound has the formula:

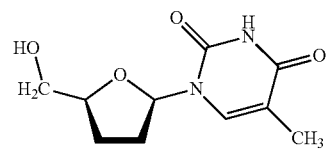

The chemical name "2',3'-dideoxyuridine" refers to a compound where uracil is linked to a pentose at the $C_1$ position of the pentose and where the pentose lacks hydroxyl groups in both the $C_2$ position and $C_3$ position. The compound has the formula:

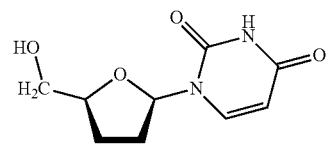

The abbreviation DMTCl refers to 4,4'-dimethoxytriphenylmethyl chloride (or, in a slightly different nomenclature, 4,4'-(chloro(phenyl)methylene)bis(methoxybenzene), which is the compound having the formula:

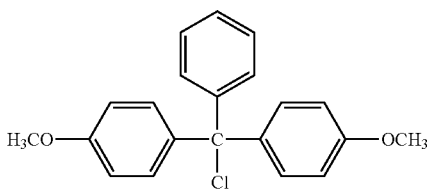 [SMILES: COc1ccc(C(Cl)(c2ccccc2)c2ccc(OC)cc2)cc1]

The chemical name "N,N-dimethylformamide dimethylacetal" refers to a compound having the formula N(CH$_3$)$_2$—CH(OCH$_3$)$_2$.

The abbreviation HBTU refers to 2-(benzotriazole-1-yl)-1,1,3,3-tetramethyluronium hexafluorophosphate having the formula:

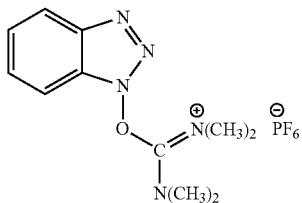

The abbreviation HBOT refers to N-hydroxybenzotriazole having the formula:

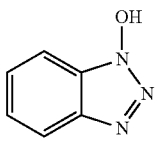

The abbreviation ADDP refers to 1,1-(azodicarbonyl) dipiperidine having the formula:

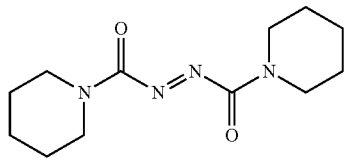 [SMILES: O=C(/N=N/C(=O)N1CCCCC1)N1CCCCC1]

The abbreviation TMSCl refers to trimethylsilyl chloride, which is the compound having the formula (CH$_3$)$_3$Si—Cl.

The abbreviation LCAA-CPG refers to long chain alkyl amine/controlled pore glass.

The term "DNA synthesis reagent #11" refers to a mixture of acetic anhydride, pyridine and tetrahydrofuran, which is a standard reagent for capping during automated oligonucleotide synthesis.

The term "DNA synthesis reagent #12" refers to a mixture of 1-methylimidazole dichloromethane and tetrahydrofuran, which is also a standard reagent for capping during automated oligonucleotide synthesis.

The term "DNA synthesis reagent #14" refers to a mixture of trichloroacetic acid and dichloromethane.

II. SELECTED EMBODIMENTS

Disclosed herein are various methods of synthesizing 2',3'-dideoxynucleoside support structures, such as 2',3'-dideoxyguanosine, 2',3'-dideoxyadenosine, 3'-deoxythymidine and 2',3'-dideoxyuridine support structures.

More particularly, according to some embodiments of the methods disclosed herein, two alternative methods for preparing a 2',3'-dideoxyguanosine support structure are provided. Each method includes several steps. In one method, the final product can be synthesized via an imide derivative of 2',3'-dideoxyguanosine.

First, according to this method 2',3'-dideoxyguanosine 1 is brought in contact and reacted with N,N-dimethylformamide dimethylacetal 2, to obtain an imide intermediate 3, which is 9-(5-(hydroxymethyl)tetrahydrofuran-2-yl)-6-oxo-6,9-dihydropurin-2-yl)-N,N-dimethyl-formimidamide. The reaction can be carried out in a suitable solvent, such as methanol. The reaction is further illustrated by the following Reaction Scheme A:

Reaction Scheme A

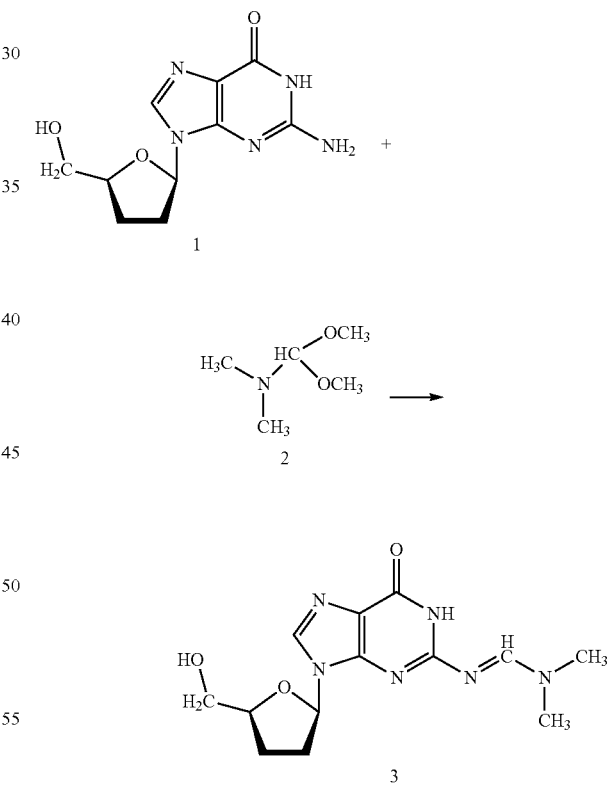

Next, the imide intermediate 3 is reacted with DMTCl 4, to obtain a second intermediate 5, which is N,N-dimethyl-N'-(6-oxo-9-(5-(((tris(4-methoxyphenyl)methoxy)methyl) tetrahydrofuran-2-yl)-6,9-dihydropurin-2-yl) formimidamide. The reaction can be carried out in a suitable solvent, such as pyridine and DMAP. The reaction is further illustrated by the following Reaction Scheme B:

Reaction Scheme B

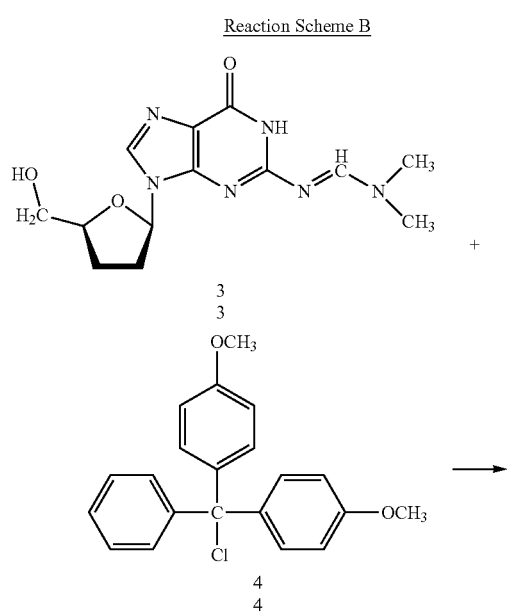

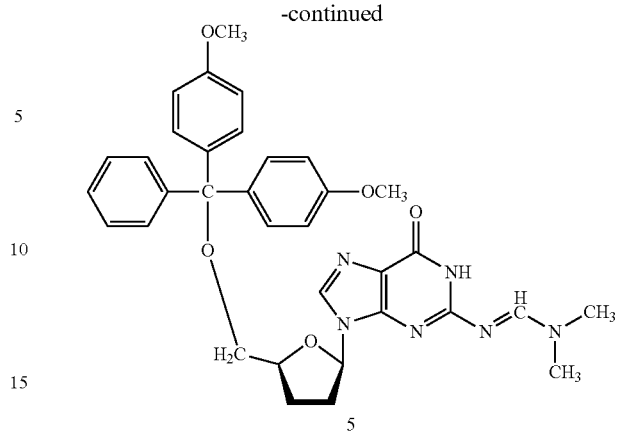

Next, the dimethylformamide protecting group is cleaved off the intermediate 5, to obtain a third intermediate 6, which is 2-amino-9-(5-(((tris(4-methoxyphenyl)methoxy)methyl) tetrahydrofuran-2-yl)-purin-6-one. An appropriate cleaving agent such as 7M ammonia in methanol can be used. The reaction is further illustrated by the following Reaction Scheme C:

Reaction Scheme C

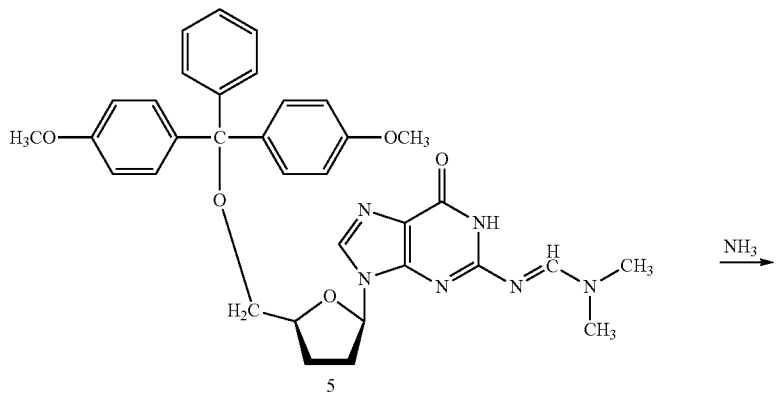

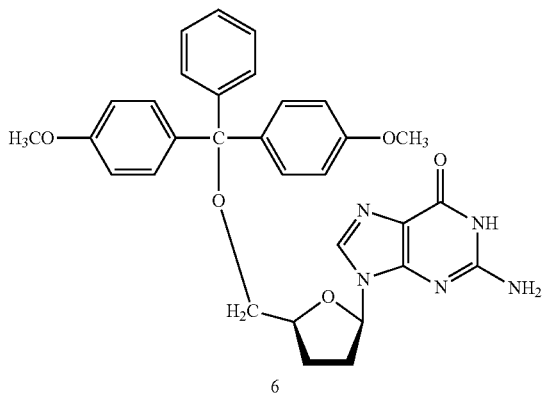

In the alternative method, the product can be synthesized via an amide derivative of 2',3'-dideoxyguanosine. First, according to this alternative method 2',3'-dideoxyguanosine 1 is brought in contact and reacted with isobutyric anhydride. The reaction can be carried out in a suitable solvent, such as pyridine, and in the presence of TMSCl, to obtain an amide intermediate 3A, which is N-(9-(5-(hydroxymethyl)tetrahydrofuran-2-yl)-6-oxo-6,9-dihydro-1H-purin-2-yl)isobutyramide. The reaction is further illustrated by the following Reaction Scheme D:

Reaction Scheme D

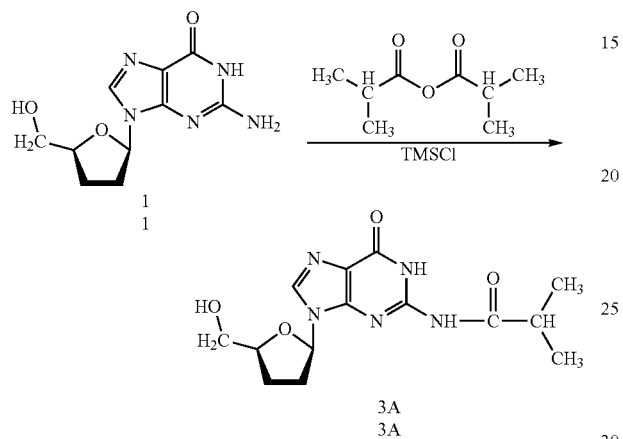

Next, the intermediate 3A is reacted with DMTCl 4, to obtain a second intermediate 5A, which is N-(9-(5-(1-(4-methoxyphenyl)-1-phenylethoxy)methyl)tetrahydrofuran-2-yl)-6-oxo-6,9-dihydro-1H-purin-2-yl)isobutyramide. The reaction can be carried out in a suitable solvent, such as pyridine and DMAP. The reaction is further illustrated by the following Reaction Scheme E:

Reaction Scheme E

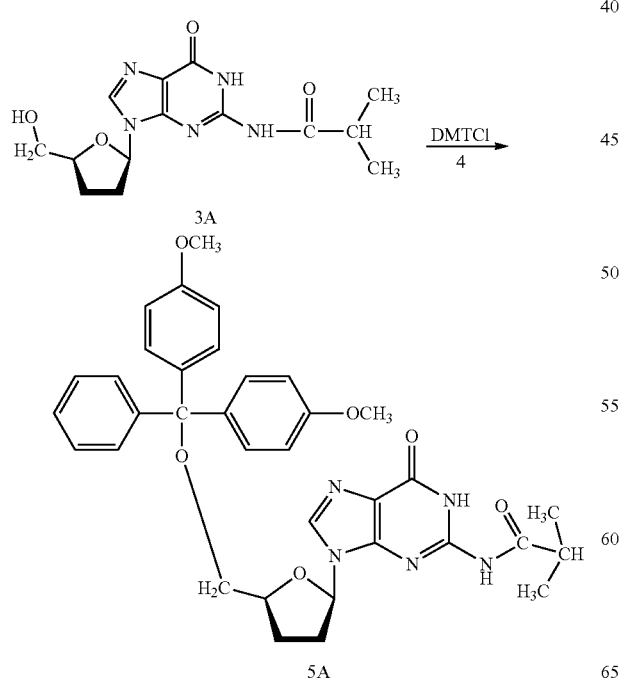

Next, the isobutyramide protecting group is cleaved off the intermediate 5A, to obtain a third intermediate 6, which is the same intermediate as the third intermediate 6 as shown in reaction scheme C. An appropriate cleaving agent such as 7M ammonia in methanol can be used. The reaction is further illustrated by the following Reaction Scheme F:

Reaction Scheme F

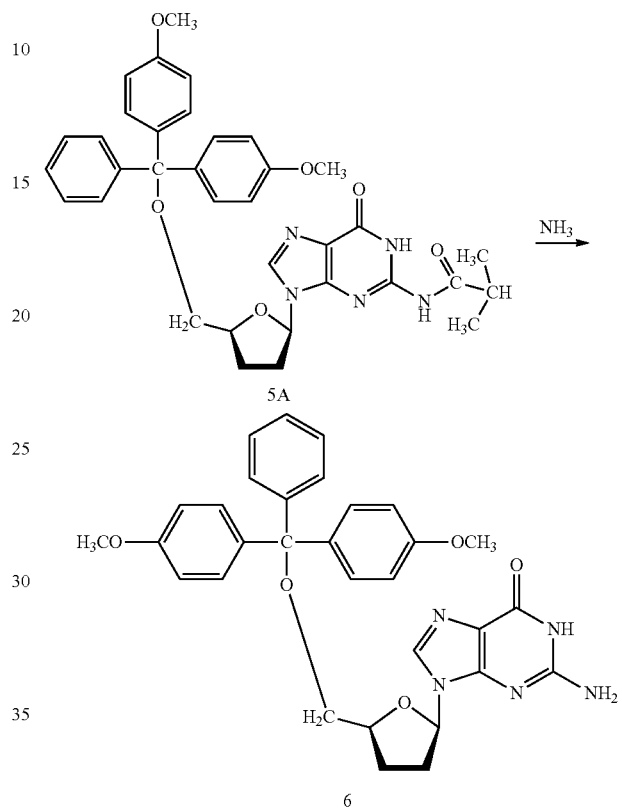

Finally, the third intermediate 6, obtained by either method discussed above (i.e., according to reaction schemes A through C or according to reaction schemes D through F) is reacted with adipic anhydride 7, to obtain a derivative of 2',3'-dideoxyguanosine 8, which is 6-oxo-6-(6-oxo-9-(5-((tris(4-methoxyphenyl)methoxy)methyl) tetrahydrofuran-2-yl)-6,9-dihydropurin-2-ylamino)hexanoic acid. The reaction can be carried out in a suitable solvent, such as pyridine, at an elevated temperature, e.g., at about 90° C. The reaction is further illustrated by the following Reaction Scheme G:

Reaction Scheme G

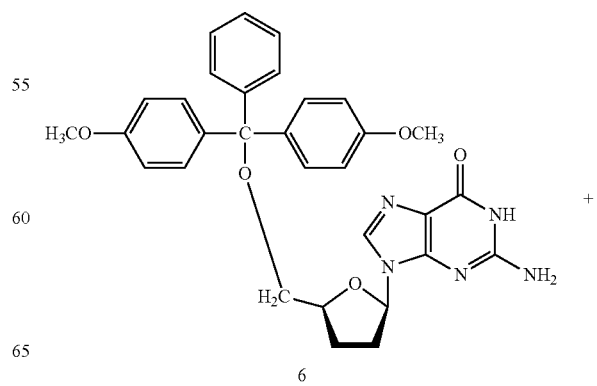

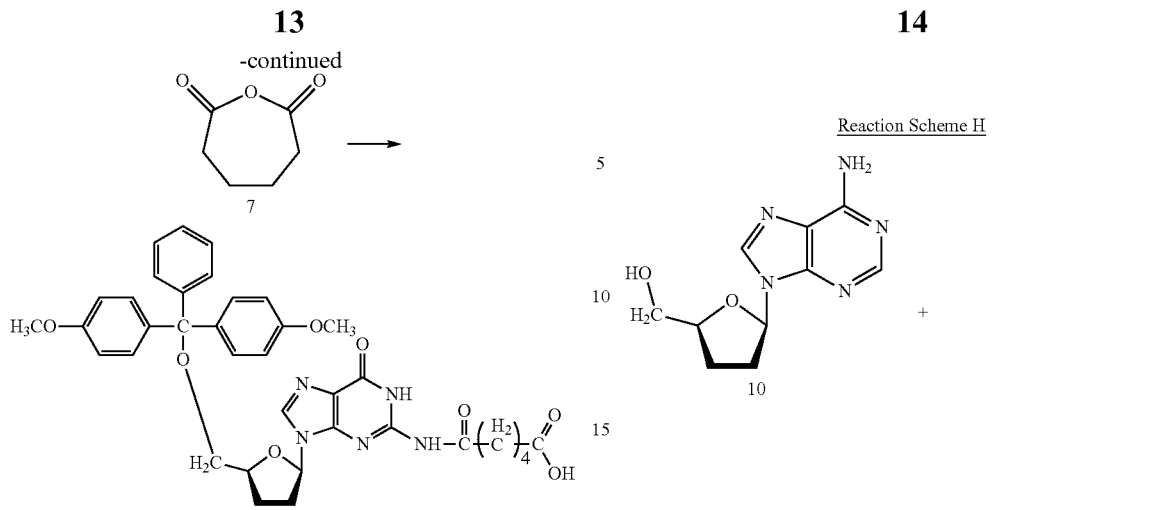

Compound 8, as shown in Reaction Scheme G, can serve as a precursor for the 2',3'-dideoxyguanosine support structure. To obtain the actual support structure, the 2',3'-dideoxyguanosine-derived compound 8 can be coupled to a suitable solid support, such as long chain alkyl amine/controlled pore glass beads (LCAA-CPG), to obtain thereby the 2',3'-dideoxyguanosine support structure 9:

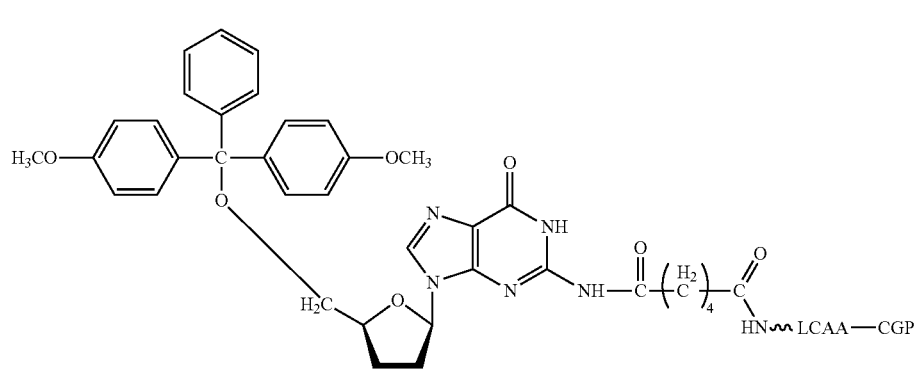

Those having ordinary skill in the art can select the optimum conditions for carrying out the process of coupling of the 2',3'-dideoxyguanosine-derived compound 8 to LCAA-CPG.

According to other embodiments of the methods disclosed herein, a method for preparing a 2',3'-dideoxyadenosine support structure is provided. The method comprises several steps. First, 2',3'-dideoxyadenosine 10 is reacted with DMTCl 11, to obtain an intermediate 12, which is 9-(5-((tris(4-methoxyphenyl)methoxy)methyl)tetrahydrofuran-2-yl)-9-purin-6-amine The reaction can be carried out in a suitable solvent, such as pyridine and DMAP (i.e., 4-dimethylaminopyridine), and in the presence of a tertiary amine, such as triethylamine The reaction is further illustrated by the following Reaction Scheme H:

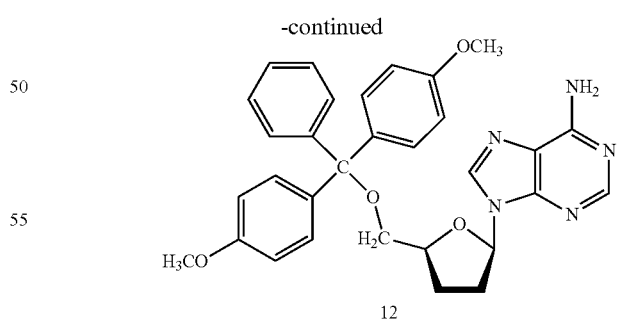

Next, pentane-1,3,5-tricarboxylic acid 13 is reacted with oxalyl chloride (also known as acryloyl chloride) 14, to obtain a cyclization product 15, which is 3-(2,6-dioxotetrahydropyran-3-yl)propanoic acid. The reaction can be carried out in a suitable solvent, such as 1,2-dichloroethane. The reaction is further illustrated by the following Reaction Scheme I:

Reaction Scheme I

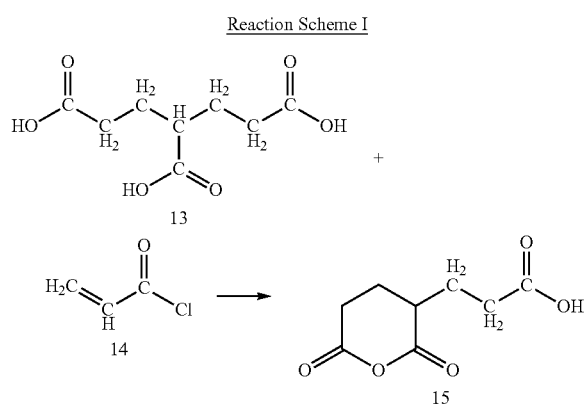

Next, the intermediate 12 (shown in Reaction Scheme H) is reacted with the product 15 (from Reaction Scheme I) to obtain a derivative of 2',3'-dideoxyadenosine 16, which is 3-(2,6-dioxo-1-(9-(5-((tris(4-methoxyphenyl)methoxy)methyl)tetrahydrofuran-2-yl)-9-purin-6-yl)piperidin-3-yl)propanoic acid. The reaction can be carried out in a suitable solvent, such as pyridine, at an elevated temperature, e.g., at about 90° C. The reaction is further illustrated by the following Reaction Scheme J:

Reaction Scheme J

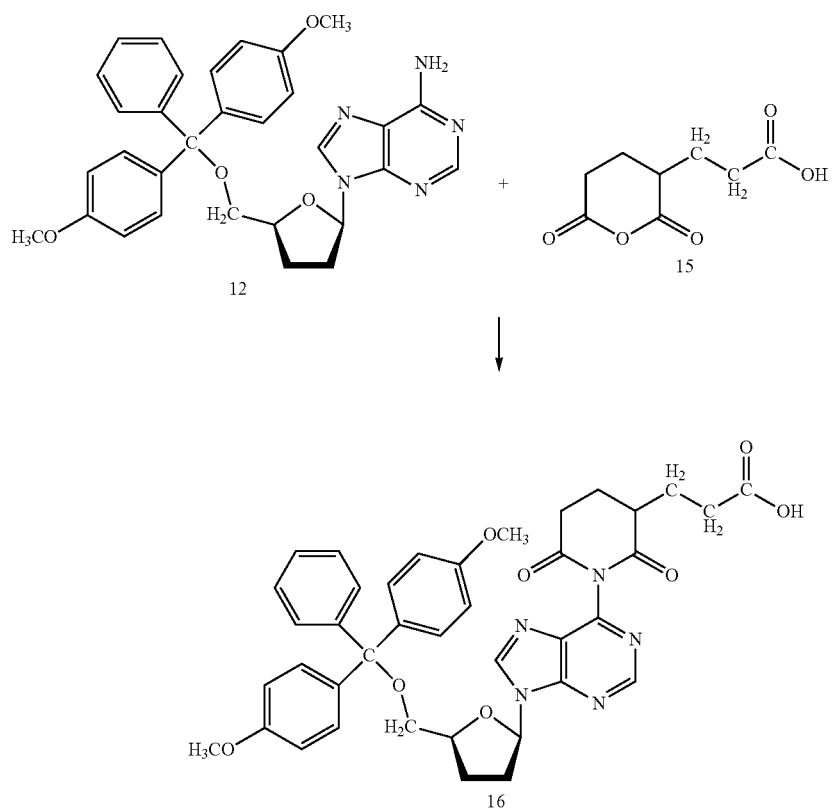

Compound 16 as shown in Reaction Scheme J can serve as a precursor for the 2',3'-dideoxyadenosine support structure. To obtain the actual support structure, the 2',3'-dideoxyadenosine-derived compound 16 can be coupled to a suitable solid support, such as long chain alkyl amine/controlled pore glass beads, to obtain thereby the 2',3'-dideoxyadenosine support structure 17:

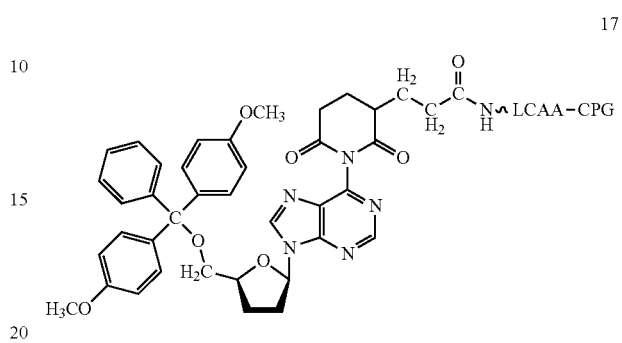

According to yet other embodiments, a method for preparing a 3'-deoxythymidine support structure is provided herein. The method includes several steps. First, 3-fluoro-6-nitrobenzoic acid 18 is reacted with trimethylsilyldiazomethane 19 to obtain a methyl ester (i.e., methyl 3-fluoro-6-nitrobenzoate) 20. This step is illustrated schematically by the following Reaction Scheme K:

Reaction Scheme K

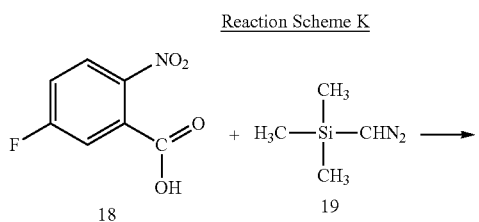

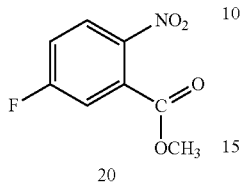

Next, the ester intermediate 20 is reacted with 2-mercaptoethanol 21. This reaction of aromatic nucleophilic substitution results in product 22 (methyl 3-(2-hydroxyethylthio)-6-nitrobenzoate), where the fluorine atom of the intermediate 20 has been displaced. This step is illustrated schematically by the Reaction Scheme L:

Reaction Scheme L

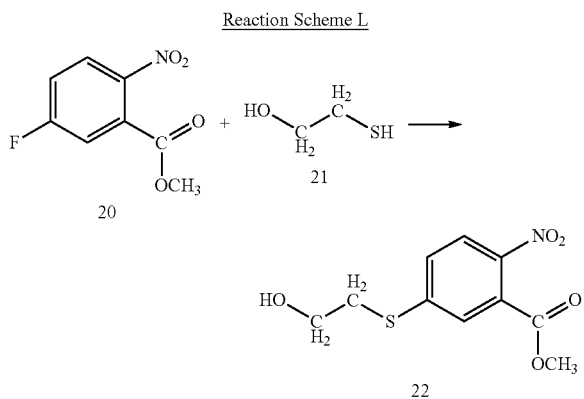

Next, 1-(5-((bis(4-methoxyphenyl)(phenyl)methoxy)methyl)tetrahydrofuran-2-yl)-5-methylpyrimidine-2,4-dione, which is the 5'-dimethoxytriphenylmethyl derivative of thymidine 23 (which can be obtained in a method similar to that shown by Reaction Scheme G and discussed above) can be treated under the Mitsunobu conditions (i.e., alkylation in the presence of ADDP and tributylphosphine in benzene) with the hydroxyl ester to alkylate the pyrimidine moiety with compound 22 exclusively at the N3 position, followed by saponification by sodium hydroxide in aqueous acetonitrile, to obtain the intermediate 24. This step is illustrated schematically by the following Reaction Scheme M:

Reaction Scheme M

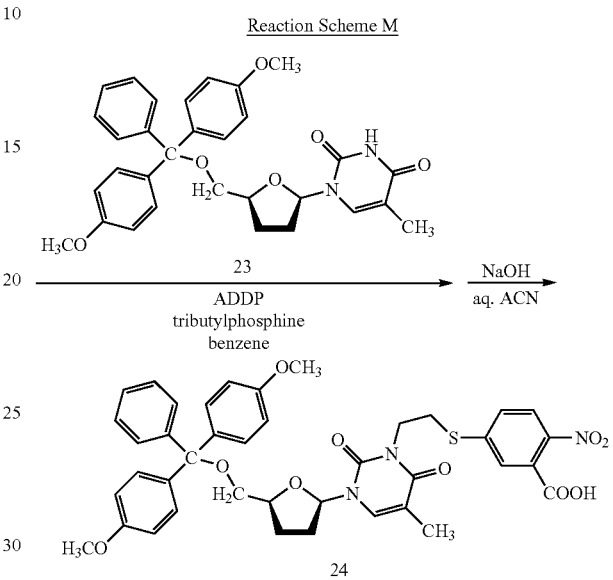

The intermediate 24 can be then coupled onto a suitable solid support, such as aminopropyl silyl-CPG, under standard conditions known to those having ordinary skill in the art, such as in the presence of HBTU/HOBT, and DIEA (i.e., diisopropylethylamine amine)/DMF. Finally, the support can be optionally capped by acetylation (e.g., with acetic anhydride $Ac_2O$ in pyridine in the presence of NMI, N-methylimidazole). The sulfide linker can then be optionally oxidized to the sulfone using the mild peroxymonosulfate-based oxidant TBA-oxone (i.e., tetrabutylammonium oxone) in dichloromethane to obtain the final product 25, which is a 3'-deoxythymidine support structure. The final stage of preparation is illustrated schematically by the following Reaction Scheme N:

Reaction Scheme N

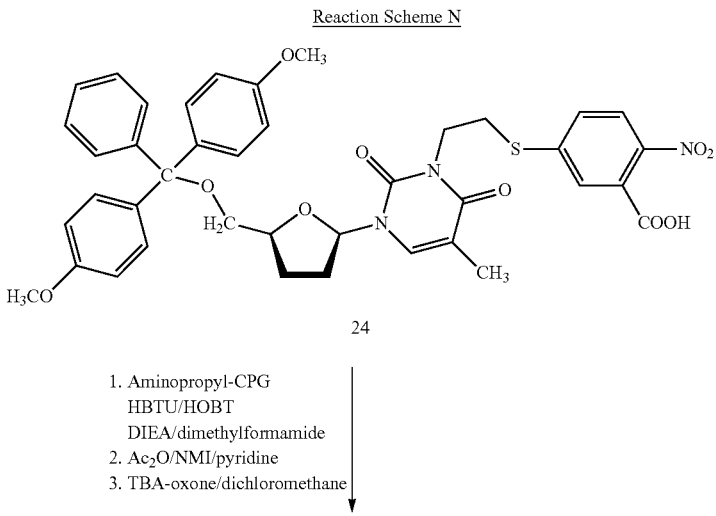

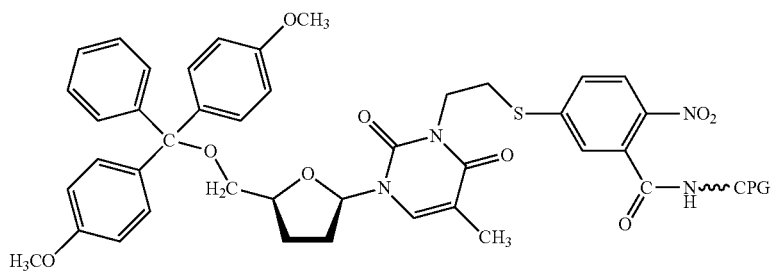

According to still other embodiments, other supports are provided herein, such as substituted 2',3'-dideoxyuridine and 3'-deoxythymidine supports based on a sulfonylethyl linker. It is envisioned that such products can be employed in standard DNA synthesis of 2',3'-dideoxyuridine-containing oligonucleotides and 3'-deoxythymidine-containing oligonucleotides which have other useful substituents on the 3'-terminal residue. Some exemplary products of this class are shown below as the general structure 25:

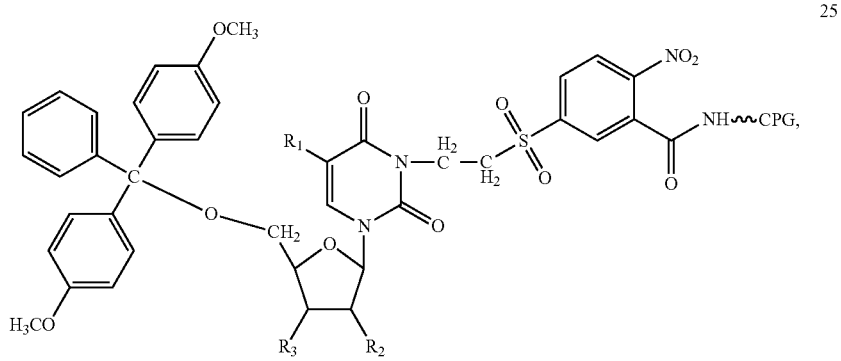

wherein each of $R_1$, $R_2$ and $R_3$ is independently H, halo, alkyl, haloalkyl, azidoalkyl, alkynylalkyl, an N-protected aminoalkyl, an S-protected thioalkyl, an O-protected hydroxyalkyl, an O-protected carboxyalkyl or carboxamidoalkyl. In one embodiment, $R_1$ is methyl and each of $R_2$ and $R_3$ is H.

One derivative of 2',3'-dideoxyuridine that can be used in the methods disclosed herein is 5-aminopropargyl-3'-ddU (5-(3-aminoprop-1-ynyl)-1-(5-(hydroxymethyl)tetrahydrofuran-2-yl)pyrimidine-2,4(1H,3H)-dione) having the formula 26 shown below:

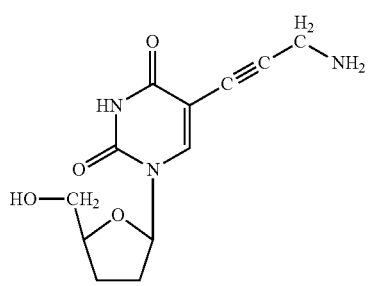

Product 26 can be used in standard DNA synthesis of 3'-ddU-containing oligonucleotides which have an amine group at the 5-position of the base, suitable for post-synthetic labeling of the oligonucleotide. One such procedure is illustrated schematically by the following Reaction Scheme O:

Reaction Scheme O

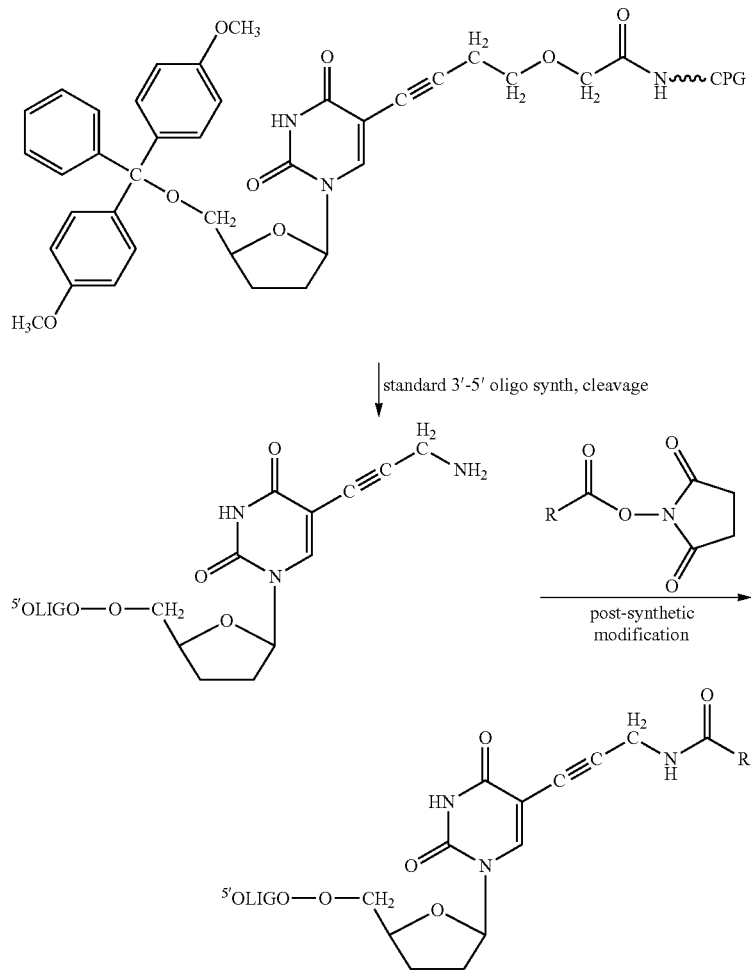

According to other embodiments, oligonucleotides labeled with 2',3'-dideoxyguanosine, with 2',3'-dideoxyadenosine, with 3'-deoxythymidine or with 2',3'-dideoxyuridine are provided herein. To obtain such labeled oligonucleotides, a 2',3'-dideoxyguanosine support structure, a 2',3'-dideoxyadenosine support structure, a 3'-deoxythymidine support structure or a 2',3'-dideoxyuridine support structure is synthesized first according to techniques described above. Any of these structures can then be used in an automated DNA synthesis process. The product of the automated DNA synthesis can be combined with a cleaving and deprotecting agent, to obtain a labeled oligonucleotide.

One having ordinary skill in the art can select an appropriate technique for performing the automated DNA synthesis. A number of methods for DNA synthesis and commercially available DNA automated synthesizers are available. Methods of DNA synthesis are reviewed in Hughes et al., *Meth. Enzymol.* 498:277-309 (2011), the content of which, including references cited therein, is incorporated herein by reference in its entirety. Methods for DNA synthesis include, without limitation, solid-phase phosphoramidite synthesis, microchip-based oligonucleotide synthesis, ligation-mediated assembly, PCR-mediated assembly, and the like. For example, such synthesis can be performed using an ABI 394 DNA Synthesizer (Applied Biosystems, Foster City, Calif.) in 0.2 μmol scale followed by standard cleavage and deprotection protocol, e.g., using 28% aqueous ammonia or a 3:1 solution of ammonia in methanol. One having ordinary skill in the art can select other cleaving agents, such as methylamine, to be used instead of, or in addition to, ammonia, if desired. The labeled oligonucleotide can then be purified using a suitable method, such as reverse phase HPLC followed by characterization of the product, e.g., by ESI-MS.

According to other embodiments, methods are provided herein for detecting a nucleic acid. Briefly, a 2',3'-dideoxynucleoside having a non-extendable 3' end which is removable by pyrophosphorolysis, is prepared first. Examples of suitable 2',3'-dideoxynucleosides include 2',3'-dideoxyguanosine, 2',3'-dideoxyadenosine, 3'-deoxythymidine and 2',3'-dideoxyuridine, which can be synthesized according to the methods described hereinabove. 2',3'-dideoxynucleoside can be used to make a 2',3'-dideoxynucleotide according to known methods.

Next, the 2',3'-dideoxynucleotide can be annealed to a nucleic acid, and the 3' non-extendable terminus of the 2',3'-dideoxynucleotide can be removed by pyrophosphorolysis. As a result, an unblocked oligonucleotide is obtained. The unblocked oligonucleotide can then be extended and the presence of the nucleic acid can be detected by detecting the extended oligonucleotide. In one embodiment, the unblocked oligonucleotide can be labeled, and the presence of the label in the extended oligonucleotide can be detected.

Both pyrophosphorolysis and the unblocked oligonucleotide extension can be optionally performed in the presence of a nucleic acid polymerase. These steps of the method of detection can be repeated a plurality of times, if desired.

Optionally, a second oligonucleotide (such as unblocked oligonucleotide) can be annealed to a complementary strand of the nucleic acid, and then the second unblocked oligonucleotide can be further extended and detected.

According to other embodiments, methods are provided herein for synthesizing a nucleic acid. A 2',3'-dideoxynucleoside (e.g., 2',3'-dideoxyguanosine, 2',3'-dideoxyadenosine, 3'-deoxythymidine or 2',3'-dideoxyuridine) having a non-extendable, removable by pyrophosphorolysis 3'-end is prepared first. The 2',3'-dideoxyguanosine, 2',3'-dideoxyadenosine, 3'-deoxythymidine, or 2',3'-dideoxyuridine can be synthesized according to the methods disclosed hereinabove. The 2',3'-dideoxynucleoside can be used to make a 2',3'-dideoxynucleotide according to known methods.

The 2',3'-dideoxynucleotide can then be annealed to a nucleic acid, and the 3' non-extendable terminus of the 2',3'-dideoxynucleotide can be removed by pyrophosphorolysis. As a result, an unblocked oligonucleotide is obtained. The unblocked oligonucleotide can then be extended in the presence of a nucleic acid nucleic acid polymerase. Pyrophosphorolysis can be also optionally performed in the presence of a nucleic acid polymerase. Both pyrophosphorolysis and extension can be repeated a plurality of times, if desired.

Optionally, a second oligonucleotide (such as unblocked oligonucleotide) can be annealed to a complementary strand of the nucleic acid, and then the second unblocked oligonucleotide can be further extended.

According to other embodiments, methods for detecting a nucleic acid can include using two oligonucleotides. According to such methods, two different 2',3'-dideoxynucleosides are prepared, each having a non-extendable 3' end, which is removable by pyrophosphorolysis, such as 2',3'-dideoxyguanosine, 2',3'-dideoxyadenosine, 3'-deoxythymidine or 2',3'-dideoxyuridine. Any of these 2',3'-dideoxynucleosides can be prepared according to the methods disclosed herein.

2',3'-dideoxynucleosides, as prepared according to the methods disclosed herein, can be used to make a 2',3'-dideoxynucleotide which can be annealed to a nucleic acid. Of the two annealed 2',3'-dideoxynucleotides, one overlaps with the other by at least one nucleotide at their respective 3' ends. Furthermore, one of the 2',3'-dideoxynucleotides anneals to a first nucleic acid strand, and the other 2',3'-dideoxynucleotide anneals to a nucleic acid strand which is the complement of the first nucleic acid strand. The 3' non-extendable terminus of the annealed first 2',3'-dideoxynucleotide and second 2',3'-dideoxynucleotide can be then removed by pyrophosphorolysis to obtain unblocked oligonucleotides, which can subsequently be extended and detected.

Both pyrophosphorolysis and the unblocked oligonucleotide extension can be optionally performed in the presence of a nucleic acid polymerase. These steps of the method of detection can be repeated a plurality of times, if desired.

Optionally, a second oligonucleotide (such as unblocked oligonucleotide) can be annealed to a complementary strand of the nucleic acid, and then the second unblocked oligonucleotide can be further extended and detected. In one embodiment, at least one of the unblocked oligonucleotides present in the extension step can contain a label and the presence of the label is detected.

According to other embodiments, methods are provided herein for detecting a nucleic acid. Briefly, a template nucleic acid is synthesized from the nucleic acid and then a 2',3'-dideoxynucleoside having a non-extendable 3' end which is removable by pyrophosphorolysis is made. Examples of suitable 2',3'-dideoxynucleosides include 2',3'-dideoxyguanosine, 2',3'-dideoxyadenosine, 3'-deoxythymidine and 2',3'-dideoxyuridine, all of which can be synthesized according to the methods disclosed herein. The 2',3'-dideoxynucleoside can be used to make a 2',3'-dideoxynucleotide according to techniques known to those having ordinary skill in the art.

Then, the 2',3'-dideoxynucleotide can be annealed to a template nucleic acid, and the 3' non-extendable terminus of the 2',3'-dideoxynucleotide can be removed by pyrophosphorolysis. As a result, an unblocked oligonucleotide is obtained. The unblocked oligonucleotide can be then extended and the presence of the nucleic acid can be detected by detecting the extended oligonucleotide. In one embodiment, the unblocked oligonucleotide can be labeled, and the presence of the label in the extended oligonucleotide can be detected.

The template nucleic acid can be obtained in a variety of ways. In one embodiment, the template nucleic acid can be synthesized by annealing to one strand of the nucleic acid a first complementary oligonucleotide that is sequence specific, followed by extending the first complementary oligonucleotide in the presence of a nucleic acid polymerase to produce an extended first oligonucleotide. A second oligonucleotide can then be added to a 3' terminus of the extended first oligonucleotide. As a result, the template nucleic acid is obtained.

The process can include some optional features. For instance, the template nucleic acid can be amplified, for example, by a polymerase chain reaction (PCR) or by a pyrophosphorolysis-activated polymerization. Both pyrophosphorolysis and the unblocked oligonucleotide extension can be optionally performed in the presence of a nucleic acid polymerase. The steps of the methods of detection can be repeated a plurality of times, if desired.

Any of several methods can be used to amplify the target nucleic acid from the sample. The term "amplifying" which typically refers to an "exponential" increase in the number of copies of the target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including, but not limited to polymerases and thermostable polymerases such as DNA polymerase, RNA polymerase and reverse transcriptase, aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art. Any in vitro means for multiplying the copies of a target sequence of nucleic acid can be utilized. These include linear, logarithmic, or any other amplification method. Exemplary methods include polymerase chain reaction (PCR; see, e.g., U.S. Pat. Nos. 4,683,202; 4,683,195; 4,965,188; and 5,035,996), isothermal procedures (using one or more RNA polymerases (see, e.g., WO 2006/081222), strand displacement (see, e.g., U.S. Pat. No. RE39, 007), partial destruction of primer molecules (see, e.g., WO 2006/087574)), ligase chain reaction (LCR) (see, e.g., Wu, et al. Genomics 4:560-569 (1990) and Barany, et al. Proc. Natl. Acad. Sci. USA 88:189-193 (1991)), Qβ RNA replicase systems (see, e.g., WO 1994/016108), RNA transcription-based systems (e.g., TAS, 3SR), rolling circle amplification (RCA) (see, e.g., U.S. Pat. No. 5,854,033; U.S. Pub. No. 2004/265897; Lizardi, et al. Nat. Genet. 19:225-232 (1998); and Barter, et al. Nucleic Acid Res. 26: 5073-5078 (1998)), and strand displacement amplification (SDA) (Little, et al. Clin. Chem. 45:777-784 (1999)), among others. Many systems are suitable for use in amplifying target nucleic acids and are contemplated herein as would be understood by one of skill in the art.

Any of several methods can be used to detect amplified target nucleic acids using primers or probes. Many different reagents, systems, or detectable labels can be used in the methods described herein. These include, for example, TaqMan® systems, detectable label-quencher systems (e.g., FRET, salicylate/DTPA ligand systems (see, e.g., Oser, et al. Angew. Chem. Int. Ed. Engl. 29:1167-1169 (1990), displacement hybridization, homologous probes, assays described in EP 070685), molecular beacons (e.g., NASBA), Scorpion, locked nucleic acid (LNA) bases (Singh, et al. Chem. Commun 4:455-456 (1998)), peptide nucleic acid (PNA) probes (Pellestor, et al. Eur. J. Hum. Gen. 12:694-700 (2004)), Eclipse probes (Afonina, et al. Biotechniques 32:940-949 (2002)), light-up probes (Svanvik, et al. Anal. Biochem. 281:26-35 (2000)), molecular beacons (Tyagi, et al. Nat. Biotechnol. 14:303-308 (1996)), tripartite molecular beacons (Nutiu, et al. Nucleic Acids Res. 30:E94 (2002)), QuantiProbes (www.qiagen.com), HyBeacons (French, et al. Mol. Cell. Probes 15:363-374 (2001)), displacement probes (Li, et al. Nucleic Acids Res. 30:E5 (2002)), HybProbes (Cardullo, et al. Proc. Natl. Acad. Sci. USA 85:8790-8794 (1988)), MGB Alert (www.nanogen.com), Q-PNA (Fiandaca, et al. Genome Res. 11:609-613 (2001)), Plexor (www.Promega.com), LUX primers (Nazarenko, et al. Nucleic Acids Res. 30:E37 (2002)), Scorpion primers (Whitcombe, et al. Nat. Biotechnol. 17:804-807 (1999)), AmpliFluor® (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products can be monitored while the reaction is in progress. An apparatus for detecting the signal generated by the detectable label can be used to detect, measure, and quantify the signal before, during, or after amplification. The particular type of signal may dictate the choice of detection method. For example, in some embodiments, fluorescent dyes are used to label probes or amplified products. The probes bind to single-stranded or double-stranded amplified products, or the dyes intercalate into the double-stranded amplified products, and consequently, the resulting fluorescence increases as the amount of amplified product increases. In some embodiments, the $T_m$ is ascertained by observing a fluorescence decrease as the double-stranded amplified product dissociates and the intercalating dye is released therefrom. The amount of fluorescence can be quantitated using standard equipment such as a spectra-fluorometer, for example. The use of other methods or reagents is also contemplated herein as would be understood by one of skill in the art.

One exemplary method for amplifying and detecting target nucleic acids is commercially available as TaqMan® (see, e.g., U.S. Pat. Nos. 4,889,818; 5,079,352; 5,210,015; 5,436,134; 5,487,972; 5,658,751; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and 7,445,900). TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (i.e., the higher the signal the greater the amount of amplification). Variations of TaqMan® assays, such as LNA™ spiked TaqMan® assay, are known in the art and would be suitable for use in the methods described herein.

One or more detectable labels or quenching agents are typically attached to a primer or probe. The detectable label can emit a signal when free or when bound to one the target nucleic acid. The detectable label can also emit a signal when in proximity to another detectable label. Detectable labels can also be used with quencher molecules such that the signal is only detectable when not in sufficiently close proximity to the quencher molecule. For instance, in some embodiments, the assay system can cause the detectable label to be liberated from the quenching molecule. Any of several detectable labels can be used to label the primers and probes used in the methods described herein. As mentioned above, in some embodiments the detectable label can be attached to a probe which can be incorporated into a primer or may otherwise bind to amplified target nucleic acid (for example, a detectable nucleic acid binding agent such as an intercalating or non-intercalating dye). When using more than one detectable label, each label should differ in its spectral properties such that the labels can be distinguished from each other, or such that together the detectable labels emit a signal that is not emitted by either detectable label alone. Exemplary detectable labels include, but are not limited to, a fluorescent dye or fluorphore (i.e., a chemical group that can be excited by light to emit fluorescence or phosphorescence), "acceptor dyes" capable of quenching a fluorescent signal from a fluorescent donor dye, and the like. Suitable detectable labels include, for example, fluorosceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY FL/BODIPY FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels can also be used (see, e.g., US Pub. No. 2009/0197254), as would be known to those of skill in the art.

According to yet other embodiments, pyrophosphorolysis-activated polymerization methods are provided herein for synthesizing a desired nucleic acid strand on a nucleic acid template strand. These methods include conducting the following steps serially. First, a 2',3'-dideoxynucleoside is prepared, e.g., 2',3'-dideoxynucleoside as 2',3'-dideoxyguanosine, 2',3'-dideoxyadenosine, 3'-deoxythymidine and 2',3'-dideoxyuridine can be used.

Any of these 2',3'-dideoxynucleosides can be prepared according to the methods disclosed herein. Then, such prepared 2',3'-dideoxynucleoside can be used to make activatable 2',3'-dideoxynucleotide having a non-extendable 3'-deoxynucleotide end, which is removable by pyrophosphorolysis and has a mismatch with respect to the corresponding nucleotide on the template strand.

The foregoing discussion discloses just some methods for preparing 2',3'-dideoxynucleotide support structures. Alternatively, other derivatives of 2',3'-dideoxynucleosides can be used for the same purpose. Some non-limiting examples of such 2',3'-dideoxynucleoside derivatives include the following compounds 27-32:

27

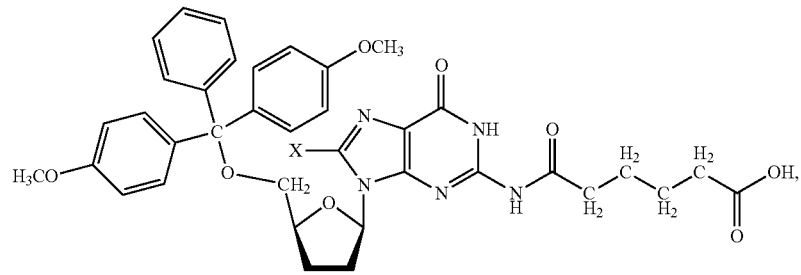

28

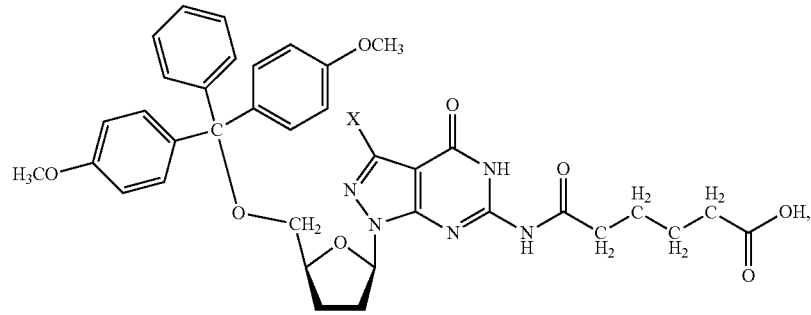

29

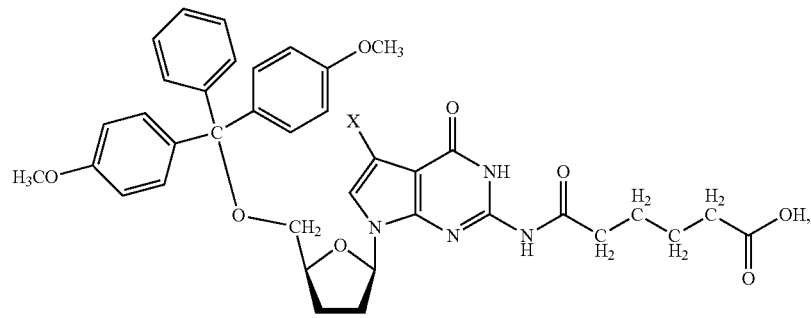

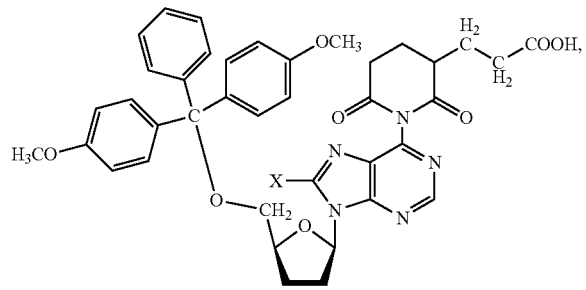

30

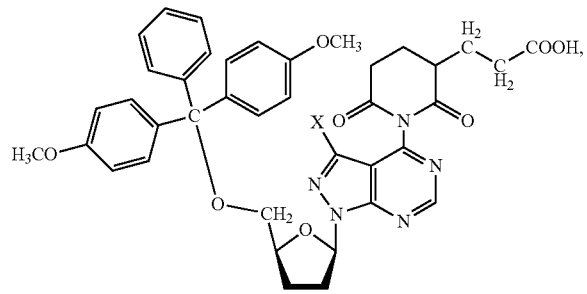

31

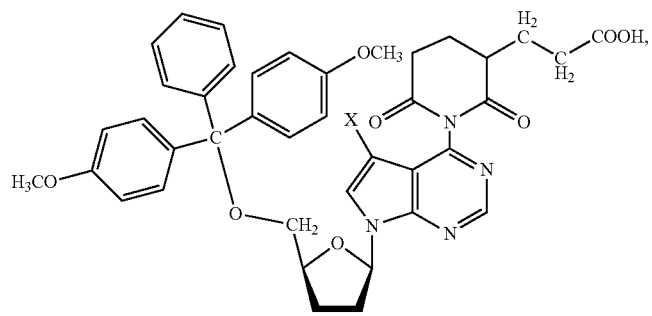

32 wherein in each of compounds 27-32, X is H, halo (Cl, Br, F or I) or any alkyl or substituted alkyl group.

The activatable 2',3'-dideoxynucleotide can then be annealed to a template nucleic acid strand followed by pyrophosphorolysis of the resulting duplex with pyrophosphate and an enzyme that has pyrophosphorolysis activity thereby activating the 2',3'-dideoxynucleotide by removal of the terminal 3'-deoxynucleotide. Finally, the step of polymerizing is performed by extending the activated 2',3'-dideoxynucleotide on the template strand in the presence of four nucleoside triphosphates and a nucleic acid polymerase to synthesize the desired nucleic acid strand.

The nucleic acid polymerase can be any compound or system that will function to accomplish the amplification of the nucleic acid. Suitable enzymes include, for example, Tfl DNA polymerase, Taq DNA polymerase, E. coli DNA polymerase I, Klenow fragment of E. coli DNA polymerase I, T4 DNA polymerase, T7 DNA polymerase, other available DNA polymerases, RNA polymerases or their variants, reverse transcriptase or its variants, and other genetically engineered versions, such as ThermoSequenase™.

III. EXAMPLES

The methods disclosed herein will be further clarified by a consideration of the following examples, which are intended to be purely exemplary and not to in any way limit the scope of the disclosure. In the synthetic examples provided below, reagents and solvents were obtained from Sigma-Aldrich (St. Louis, MO.) except for 3'-deoxy-5'-O-(4,4'-dimethoxytrityl)thymidine which was obtained from Berry & Assoc., Dexter, Mich. Column flash chromatography utilized 60-200 mesh silica gel (J.T. Baker). NMR spectra were recorded on a Bruker 400 MHz instrument. MS data were obtained on an AB-Sciex API-150 (electrospray) or AB-Voyager 6274 (MALDI-TOF).HPLC analyses were performed on an Agilent 1100 (DAD) with Waters C18-MS column at 60C, running a gradient of 7-50% acetonitrile in 0.1M triethylammonium acetate, pH 6.8.

Example 1

Preparation of A 2',3'-Dideoxyadenosine Support Structure

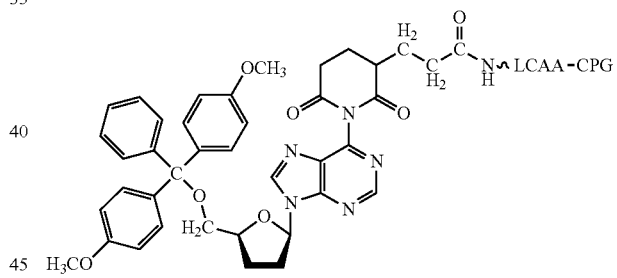

9-(5-(((tris(4-methoxyphenyl)methoxy)methyl)tetrahydrofuran-2-yl)-9-purin-6-amine (product 12 in Reaction Scheme H, above) was synthesized first according to the reaction shown by Reaction Scheme H. To obtain this compound, 2',3'-dideoxyadenosine (500 mg, 2.13 mmol) was dried three times by co-evaporation with pyridine, and suspended in about 10 mL of dry pyridine, were added DMTCl (1.084 g, 3.2 mmol), triethylamine (0.45 mL, 3.2 mmol) and DMAP 6.48 mg, 0.053 mmol) were added. This reaction mixture was stirred at room temperature for about 4 hours, and then about 10 mL of 5% NaHCO₃ were added.

The mixture was then extracted with two ~30 mL portions of ethyl acetate, followed by combining the organic layers and by evaporation to dryness. The residue was purified by flash chromatography on silica gel (CH₂Cl₂/CH₃OH=10/1), to create product 12, i.e., 9-(5-(((tris(4-methoxyphenyl) methoxy)methyl)tetrahydrofuran-2-yl)-9-purin-6-amine.

Yield 468 mg (41%). Product 12 was then used in the subsequent steps of preparation.

Next, about 100 mg (0.186 mmol) of product 12 (obtained as described above) was combined with about 139 mg (0.746 mmol) of 3-(2,6-dioxotetrahydropyran-3-yl)propanoic acid (product 15 in reaction scheme I). Then about 5 mL of anhydrous pyridine was added and the mixture was stirred for about 6 hours at about 90° C.

After evaporation, the residue was diluted with about 200 mL of methylene chloride, washed with 10% icy citric acid (5° C.) and then with ice water. After drying, the organic layer was evaporated and the residue was chromatographed on silica gel ($CH_2Cl_2/CH_3OH=10/1$) to obtain 3-(2,6-dioxo-1-(9-(5-(((tris(4-methoxyphenyl)methoxy)methyl)tetrahydrofuran-2-yl)-9-purin-6-yl)piperidin-3-yl)propanoic acid (14 mg, 11%), which is product 16 in Reaction Scheme J.

Product 16 was then used in the final stage of the process. About 14 mg (0.0198 mmol) of product 16 was combined with N,N-diisopropylethylamine (so called Hünig's base) (about 5.2 mL or 0.0297 mmol), HBTU (about 7.5 mg or 0.0198 mmol) and LCAA-CGP (about 417 mg or 0.0158 mmol). The mixture was shaken at room temperature for about 2 hours, followed by washing twice with dimethylformamide and twice with tetrahydrofuran, to create the final 2',3'-dideoxyadenosine support structure (product 17 above).

Example 2

Preparation of A 2',3'-Dideoxyguanosine Support Structure dissolved in about 30 mL of dry pyridine, DMTCl (about 1.9 g, 5.6 mmol) was added. This reaction mixture was stirred at room temperature overnight under an argon blanket, and then about 100 mL of saturated $NaHCO_3$ were added.

The mixture was then extracted with three ~100 mL portions of methylene chloride, followed by separating the organic layer and by drying over anhydrous $Na_2SO_4$. The solvent was evaporated under reduced pressure, and the residue was purified by chromatography on silica gel ($CH_2Cl_2/CH_3OH=10/1$), to create product 5. Yield about 1.9 g (83% for the two steps). Product 5 was then used in the subsequent steps of preparation.

Product 5, as shown by the Reaction Scheme B and obtained as described above, was then used to obtain 2-amino-9-(5-((tris(4-methoxyphenyl)methoxy)methyl)tetrahydrofuran-2-yl)-purin-6-one (compound 6 in Reaction Schemes C and F). To that end, about 200 mg (0.329 mmol) of product 5, as shown by Reaction Scheme B and obtained as described above, was dissolved in about 10 mL of 7M ammonia in methanol. The reaction mixture was stirred for about 12 hours at room temperature. The solvent was evaporated and the residue was analyzed by mass-spectometry and dried in a vacuum, to create product 6 as shown in Reaction Schemes C and F. Product 6 was then used in the subsequent steps of preparation, without further preliminary purification.

About 100 mg (0.18 mmol) of compound 6, as shown in Reaction Schemes C and F and obtained as described above,

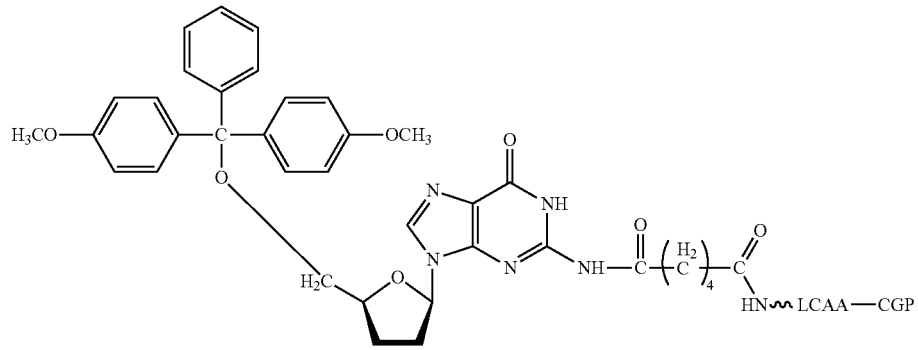

9-(5-(hydroxymethyl)tetrahydrofuran-2-yl)-6-oxo-6,9-dihydropurin-2-yl)-N,N-dimethylformimidamide amine (product 3 in Reaction Scheme A, above) was synthesized first according to the reaction shown by Reaction Scheme A. To obtain this compound, 2',3'-dideoxyguanosine (about 947 mg, 3.77 mmol) was dissolved in 20 mL of methanol and N,N-dimethylformamide dimethyl acetal (about 1.06 mL, 7.98 mmol) was added. The mixture was stirred overnight at room temperature followed by adding another portion of N,N-dimethylformamide dimethyl acetal (about 0.5 mL, 3.9 mmol). The mixture was again stirred for about 2 hours at room temperature. The solvent was evaporated to yield the product, (compound 3 in Reaction Scheme A, above) as a white solid.

Next, compound 3 as shown in reaction scheme A was used to obtain N,N-dimethyl-N'-(6-oxo-9-(5-((tris(4-methoxyphenyl) methoxy)methyl)tetrahydrofuran-2-yl)-6,9-dihydropurin-2-yl) formimidamide (product 5 on the Reaction Scheme B), according to the above-shown Reaction Scheme B. To this end, compound 3 as shown in Reaction Scheme A and obtained as described above, was dried three times by co-evaporation with pyridine, and was co-evaporated three times with anhydrous pyridine, and then suspended in about 10 mL of anhydrous pyridine. To this suspension, about 185 mg (1.45 mmol) of adipic anhydride (compound 7 in Reaction Scheme G) were added, and the reaction mixture was stirred at about 90° C. for about 24 hours. The solution was concentrated and the residue was dissolved in about 70 mL of methylene chloride and washed with a 10% aqueous solution of citric acid (about 20 mL) and water (also about 20 mL). The organic layer was dried over anhydrous $Na_2SO_4$ and the solvent was evaporated under reduced pressure. The residue was flash chromatographed on silica gel to create 6-oxo-6-(6-oxo-9-(5-((tris(4-methoxyphenyl) methoxy)methyl)tetrahydrofuran-2-yl)-6,9-dihydropurin-2-ylamino)hexanoic acid (yield about 54 mg, 44%), which is product 8 in the Reaction Scheme G.

Product 8 was then used in the final stage of the process. About 44 mg (0.064 mmol) of product 8 was combined with N,N-diisopropylethylamine (about 45 mL or 0.26 mmol), HBTU (about 49 mg or 0.13 mmol) and LCAA-CGP (about 865 mg or 0.032 mmol). The mixture was shaken at room temperature for about 4 hours, followed by washing twice with dimethylformamide and twice with tetrahydrofuran, to create the final 2',3'-dideoxyguanosine support structure (product 9 above).

Example 3

Preparation of N-(9-(5-(1-(4-methoxyphenyl)-1-phenylethoxy)methyl)tetrahydrofuran-2-yl)-6-oxo-6,9-dihydro-1H-purin-2-yl)isobutyramide

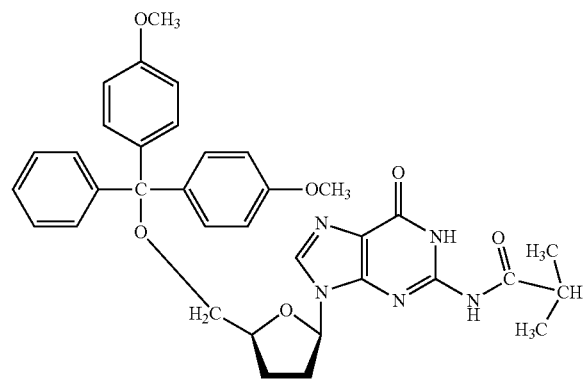

Compound 5A shown in Reaction Schemes E and F, above, can be used for preparing compound 6 shown in Reaction Schemes C and F, instead of compound 5 discussed in Example 2, above. The synthesis was carried out according to the reaction showin by Reaction Scheme D. 2',3'-dideoxyguanosine was co-evaporated with anhydrous pyridine three times before it was suspended in about 20 mL of dry pyridine. Trimethylchlorosilane (about 1.6 mL, 12.4 mmol) was added and the reaction mixture was stirred at room temperature for about 15 minutes, followed by adding about 2.6 mL (15.5 mmol) isobutyric anhydride. The reaction mixture was kept overnight at room temperature, followed by cooling in an ice bath and adding about 4 mL of water after about 5 minutes. Then, about 4 mL of about 29% aqueous ammonia was added and the reaction was stirred for about 15 minutes. The resulting solution was evaporated to dryness, and the residue was dissolved in about 20 mL of water, followed by washing using ethylacetate/ethyl ether system (1/1). The organic layer was extracted using about 10 mL of water, and the combined aqueous layers were concentrated to about 10 mL. As a result of this procedure, the intermediate N-(9-(5-(hydroxymethyl)tetrahydrofuran-2-yl)-6-oxo-6,9-dihydro-1H-purin-2-yl)isobutyramide (product 3A in Reaction Schemes D and E), was obtained, which was then used in the final step of preparation, without further preliminary purification.

Product 3A, obtained as described above, was co-evaporated with anhydrous pyridine three times before it was suspended in about 10 mL of dry pyridine. DMTCl (about 2.1 g, 6.2 mmol) and DMAP (about 57 mg, 047 mmol) were added and the reaction was stirred at room temperature overnight. About 20 mL of aqueous $NaHCO_3$ were added and the solution was then extracted with two about 80 mL portions of methylene chloride. The combined organic layers were dried and evaporated to dryness, followed by purifying the residue by flash chromatography on silica gel, to afford N-(9-(5-(1-(4-methoxyphenyl) -1-phenylethoxy) methyl)tetrahydrofuran-2-yl)-6-oxo-6,9-dihydro-1H-purin-2-yl)isobutyramide (the title product 5A in Reaction Schemes E and F). The yield was about 320 mg.

Example 4

Automated DNA Synthesis Using A 2',3'-Dideoxyadenosine Support Structure

Using an automated DNA synthesis procedure, oligonucleotides labeled with 2',3'-dideoxyadenosine were obtained. The process was initiated by a preparatory step, at which the 2',3'-dideoxyadenosine support structure obtained as described in Example 1 was combined with DNA synthesis reagents #11 and #12 (about 1 mL of each). The mixture was shaken at room temperature for about 1 hour and washed with tetrahydrofuran, methyl cyanide and methylene chloride, and dried under vacuum.

A loading test was conducted next. To about 15 mg of 2',3'-dideoxyadenosine support structure in a 50 mL flask, was added about 4 ml of DNA synthesis reagent #14 and methylene chloride to the 50 mL mark. Absorption was measured at 498 nm using methylene chloride as a blank. The result was that $A_{498\ nm}$ was 0.385. Accordingly, loading was calculated as 18.3 µmol/g ($0.385 \times 50 \times 10^6 / 70 \times 10^3 \times 15$).

The synthesis was carried out on an ABI 394 DNA Synthesizer in 0.2 µmol scale. 7M aqueous ammonia in methanol (3/1) was used as the cleaving agent. The product was subjected to HPLC, extraction and collection, followed by drying in vacuum. The product was then dissolved in 200 nL of water to make the stock solution. 5 nL of the stock solution were then dissolved in 200 nL of water and absorption at 260 nm was measured. In two parallel experiments $A_{260\ nm}$ was 0.407 and 0.368 corresponding to 56 µM of the oligonucleotide.

Example 5

Automated DNA Synthesis Using a 2',3'-Dideoxyguanosine Support Structure

Using an automated DNA synthesis procedure, oligonucleotides labeled with 2',3'-dideoxyguanosine were obtained. The process was initiated by a preparatory step, at which the 2',3'-dideoxyguanosine support structure obtained as described in Example 2 was combined with DNA synthesis reagents #11 and #12 (about 1 mL of each). The mixture was shaken at room temperature for about 1 hour and washed twice with tetrahydrofuran, twice with methyl cyanide and twice with methylene chloride, followed by drying under vacuum.

A loading test was conducted next. To about 16 mg of 2',3'-dideoxyguanosine support structure in a 50 mL flask, was added about 4 ml of DNA synthesis reagent #14 and methylene chloride to the 50 mL mark. Absorption was measured at 498 nm using methylene chloride as a blank. The result was that $A_{498\ nm}$ was 0.367. Accordingly, loading was calculated as 16 µmol/g ($0.367 \times 50 \times 10^6 / 70 \times 10^3 \times 15$).

The synthesis was carried out on an ABI 394 DNA Synthesizer in 0.2 µmol scale. 7M aqueous ammonia in methanol (3/1) was used as the cleaving agent. The product was subjected to HPLC, extraction and collection, followed by drying under a vacuum. The product was then dissolved in 200 nL of water to make the stock solution. The following oligonucleotides labeled with 2',3'-dideoxyguanosine were obtained: $AGTF_bG$, $AGTR_bG$, $AGTF_{dd}G$, and $AGTR_{dd}G$.

Example 6

Preparation of a 3'-Deoxythymidine Support Structure

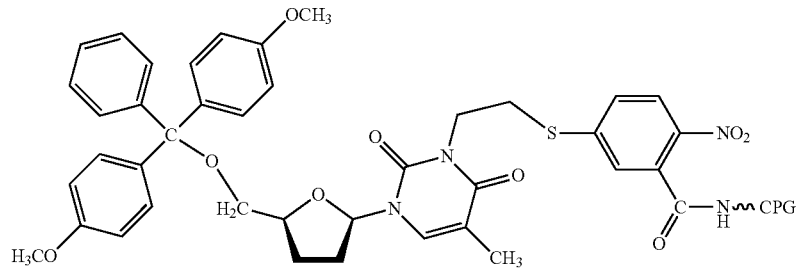

Methyl 3-fluoro-6-nitrobenzoate (i.e., compound 20 in Reaction Scheme K above) was synthesized first. To obtain this compound, about 1.0 g (5 4 mmol) of 3-fluoro-6-nitrobenzoic acid was dissolved in methanol (about 25 mL) and toluene (25 mL). To this was added, dropwise with swirling over 10 minutes, about 7.35 mL (14.7 mmol) of a 2M solution of trimethylsilyldiazomethane in hexane. Bubbling ensued, with yellow color dissipating until final addition. The solution was stirred for about 90 min, then acetic acid was added (about 650 µL) until the color dissipated and bubbling ceased.

After stirring for about 1 hour, the solution was evaporated and dried under vacuum to produce the product as a yellow oil. The yield was about 1.07 g (100%). $^1$H-NMR (CDCl$_3$): δ 8.02 (dd, 1H), δ 7.37 (d, 1H), δ 7.30 (m, 1H), δ 3.94 (s, 3H). $^{19}$F NMR (CDCl$_3$): δ −102.28 (m).

Next, a solution of about 200 mg of methyl 3-fluoro-6-nitrobenzoate (1.0 mmol) obtained as described above in acetonitrile (about 1.5 mL) was treated with about 105 µL of 2-mercaptoethanol (1.5 mmol), as shown in Reaction Scheme L above. About 207 mg of anhydrous K$_2$CO$_3$ (1.5 mmol) was added and the mixture was stirred at about 25° C. After 2 days the reaction was filtered through celite and filtrate evaporated.

The residue was dissolved in about 20 mL of ethyl acetate, washed three times with 5% aqueous Na$_2$CO$_3$, then with saturated NaCl, and the organic phase was evaporated and dried under a vacuum to produce methyl 3-(2-hydroxyethylthio)-6-nitrobenzoate (compound 22 in reaction scheme L above) as a yellow oil, >95% pure. The yield was about 215 mg, (84%). $^1$H-NMR (CDCl$_3$): δ 7.91 (d, 1H), δ 7.49 (s, 1H), δ 7.47 (s, 1H), δ 3.93 (s, 3H), δ 3.89 (t, 2H), δ 3.25 (t, 2H), δ 2.00 (br s, 1H).

As the next step, about 151 mg (0.286 mmol) of 3'-deoxy-5'-O-(4,4'-dimethoxytrityl)thymidine (i.e., compound 23 in Reaction Scheme M above) was dissolved in about 4 mL of dry benzene and stirred in an ice bath under argon. To this was added a solution of about 100 mg (0.39 mmol) of methyl 3-(2-hydroxyethylthio)-6-nitrobenzoate obtained as described above in about 1 mL of benzene. Next, about 120 µL (0.49 mmol) of tri-n-butylphosphine was added. After stirring for about 10 minutes, the thickened mixture was allowed to come to ambient temperature, and then diluted with about 1 mL of benzene until freely stirring, followed by adding about 124 mg (0.49 mmol) of ADDP and stirring for about 18 hours. The reaction mixture was evaporated and the residue was dissolved in about 20 mL of ethyl acetate and washed 3 times with water, then with saturated aqueous solution of NaCl, and dried over Na$_2$SO$_4$.

An oily product was obtained which was purified by silica chromatography (0-5% methanol in dichloromethane, 1% triethylamine), to yield about 167 mg (76%) of the >90% pure (by NMR) waxy white solid product, methyl 5-(2-(3-(5-((bis(4-methoxyphenyl)(phenyl)methoxy)methyl)tetrahydrofuran-2-yl)-5-methyl-2,6-dioxo-2,3-dihydropyrimidin-1(6H)-yl)ethylthio)-2-nitrobenzoate. $^1$H-NMR (CD$_2$Cl$_2$): δ 7.95 (d, 1H), δ 7.68 (dd, 1H), δ 7.65 (dd, 1H), δ 7.55 (s, 1H), δ 7.45 (dd, 2H), δ 7.35-7.22 (m, 2H), δ 6.84 (d, 4H), δ 6.10 (dd, 1H), δ 4.27-4.16 (m, 3H), δ 3.92 (s, 3H), δ 3.78 (s, 6H), δ 3.40 (dd, 1H), δ 3.32-3.24 (m, 3H), δ 2.40 (m, 1H), δ 2.13-2.00 (m, 3H), δ 1.55 (s, 3H).

A solution of about 30 mg (0.039 mmol) of methyl 5-(2-(3-(5-((bis(4-methoxyphenyl)(phenyl)methoxy)methyl)tetrahydrofuran-2-yl)-5-methyl-2,6-dioxo-2,3-dihydropyrimidin-1(6H)-yl)ethylthio)-2-nitrobenzoate obtained as described above in about 1 mL of acetonitrile was treated with about 330 µL (0.33 mmol) of 1N aqueous solution of NaOH, followed by stirring for about 5 hrs and by diluting with about 5 mL of 1M aqueous solution of triethylammonium acetate (pH 7) and about 5 mL of 1M aqueous solution of sodium acetate (pH 6). The product was extracted with about 20 mL of ethyl acetate and washed 3 times with water, then with a saturated aqueous solution of NaCl. A small amount of triethylamine was added to the ethyl acetate extract and the solvent was evaporated to give an oil which solidified upon standing.

The solid was dissolved in dry acetonitrile (1% triethylamine) and filtered to remove insoluble salts. Upon drying, the filtrate gave the product as the triethylammonium salt of the acid, 5-(2-(3-(5-((bis(4-methoxyphenyl)(phenyl)methoxy)methyl)tetrahydrofuran-2-yl)-5-methyl-2,6-dioxo-2,3-dihydropyrimidin-1(6H)-yl)ethylthio)-2-nitrobenzoic acid (product 24 in Reaction Scheme M). The yield was about 20 mg (77%). MS (ESI): [M−H]−=752.4.

Product 24 was then used in the final stage of the process. A solution was prepared in DMF (about 0.5 mL) containing HBTU (about 7.5 mg, 19.8 µmol), HOBt (about 2.7 mg, 19.9 µmol), and DIEA (about 8.8 µL, 50 µmol). The solution was allowed to stand about 10 minutes and then added to a solution of about 20 mg (23 mmol) of the triethylammonium salt of product 24, obtained as described above, in about 0.5 mL of dimethylformamide. After stirring for about 10 minutes, the reaction was added to a slurry of about 311 mg (37 µmol amine/g) of aminopropyl-CPG in about 1.2 mL of dimethylformamide and then shaken gently for about 21 hours. The CPG was collected on a glass frit, then washed with dimethylformamide and dichloromethane and then dried. Next, the CPG was treated with acetic anhydride (excess) in tetrahydrofuran containing pyridine and 1-methylimidazole, for about 20 minutes, to cap any free amines on the support. The CPG was then filtered and washed with tetrahydrofuran, dichloromethane, and then dried. Finally, the sulfide linker was oxidized to the sulfone by treatment of the CPG with a solution of about 200 mg of TBA-oxone in about 2 mL of dichloromethane.

After gentle shaking for about 18 hours, the CPG was filtered, washed with dichloromethane, and dried to yield about 300 mg of activated title product, i.e., 3'-deoxythymidine support structure. Detritylation and UV-Vis quantitation of a sample of CPG gave a loading of about 18.3 μmol/g (50%).

Example 7

Automated DNA Synthesis Using a 3'-Deoxythymidine Support Structure

About 10.9 mg (200 nmol dT) of the 3'-deoxythymidine support structure obtained as described in Example 6, was packed into DNA synthesis columns for the ABI 394 DNA Synthesizer. Two representative sequences having similar GC content (near 50%) selected from a set of 3'-dT primers were prepared: (1) 24 mer, GAT CCA GAT GTT AGG GCA GTC TC(dT) (SEQ ID NO: 1), (2) 23 mer, TAT CAG TGG AGA TCC TGG ACC A(dT) (SEQ ID NO: 2). Instrument synthesis protocol was standard and coupling times were not adjusted. Final detritylation was performed on the instrument. Cleavage of DNA from support was unaccomplished under standard conditions: CPG was removed from the column and treated with 28% $NH_4OH$ in a sealed vial for 4.5 hrs at 60 C. The CPG was filtered and washed with water and the filtrate was dried under vacuum. The soluble residue was redissolved in 0.3M NaCl and the oligonucleotide isolated by ethanol precipitation.

Crude products, obtained in 85% yield, were further purified by RP-HPLC for analysis. MS (MALDI-TOF): (1) 24 mer, MW calc=7367.1, MS found=7366.1 [M–H]–, (2) 23 mer, MW calc=7047.5, MS found=7047.1 [M–H]–.

Although only a few embodiments have been described in detail and exemplified above, it is understood that many modifications are possible in the described embodiments without departing from the teachings thereof. All such modifications are intended to be encompassed within the following claims.

What is claimed is:

1. A method for preparing a 2',3'-dideoxyadenosine support structure, the method comprising:
   (a) reacting 2',3'-dideoxyadenosine with 4,4-dimethoxytriphenylmethyl chloride to obtain a first intermediate;
   (b) reacting pentane-1,3,5-tricarboxylic acid with oxalyl chloride to obtain a second intermediate;
   (c) reacting the first intermediate with the second intermediate to obtain a 2',3'-dideoxyadenosine derivative; and
   (d) coupling the 2',3'-dideoxyadenosine derivative to a solid support, thereby obtaining the 2',3'-dideoxyadenosine support structure.

2. A method for preparing an oligonucleotide labeled with 2',3'-dideoxyadenosine, the method comprising:
   (a) synthesizing the 2',3'-dideoxyadenosine support structure according to the method of claim 1;
   (b) conducting an automated DNA synthesis using said 2',3'-dideoxyadenosine support structure; and
   (c) combining the product of the automated DNA synthesis with a cleaving and deprotecting agent selected from the group consisting of ammonia and methylamine, to thereby obtain the oligonucleotide labeled with 2',3'-dideoxyadenosine.

3. The method of claim 1, wherein the solid support is aminopropylsilyl glass.

4. The method of claim 3, wherein the aminopropylsilyl glass is controlled pore glass.

5. The method of claim 1, wherein the solid support is glass beads.

6. The method of claim 5, wherein the glass beads are long chain alkyl amine controlled pore glass beads.

7. The method of claim 2, wherein the oligonucleotide is configured to have a preselected sequence to hybridize to a nucleic acid.

8. The method of claim 2, wherein the oligonucleotide is configured to be activatable by pyrophosphorolysis for subsequent extension by a polymerase.

9. The method of claim 2, wherein the oligonucleotide comprises 8 to 40 nucleoside monomeric units linked by phosphodiester linkages.

10. The method of claim 9, wherein the phosphosdiester linkages are selected from the group consisting of phosphodiester, phosphorothioate, phosphorodithioate, phosphoroselenoate, phosphorodiselenoate, phosphoroanilothioate, phosphoranilidate, and phosphoramidite.

11. A method for preparing an oligonucleotide labeled with 2',3'-dideoxyadenosine, the method comprising:
    (a) preparing the 2',3'-dideoxyadenosine support structure according to the method of claim 1;
    (b) conducting an automated DNA synthesis using said 2',3'-dideoxyadenosine support structure; and
    (c) combining the product of the automated DNA synthesis with a cleaving and deprotecting agent selected from the group consisting of ammonia and methylamine, thereby obtaining the oligonucleotide labeled with the oligonucleotide labeled with 2',3'-dideoxyadenosine.

12. The method of claim 11, wherein the oligonucleotide is configured to have a preselected sequence to hybridize to a nucleic acid.

13. The method of claim 11, wherein the oligonucleotide is configured to be activatable by pyrophosphorolysis for subsequent extension by a polymerase.

14. The method of claim 11, wherein the oligonucleotide comprises 8 to 40 nucleoside monomeric units linked by phosphodiester linkages.

15. The method of claim 14, wherein the phosphosdiester linkages are selected from the group consisting of phosphodiester, phosphorothioate, phosphorodithioate, phosphoroselenoate, phosphorodiselenoate, phosphoroanilothioate, phosphoranilidate, and phosphoramidite.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (24)..(24)
<223> OTHER INFORMATION: n = dT

<400> SEQUENCE: 1
gatccagatg ttagggcagt ctcn                                    24

<210> SEQ ID NO 2
<211> LENGTH: 23
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (23)..(23)
<223> OTHER INFORMATION: n = dT

<400> SEQUENCE: 2
tatcagtgga gatcctggac can                                     23